United States Patent [19]

Emerson et al.

[11] Patent Number: 5,792,467
[45] Date of Patent: Aug. 11, 1998

[54] REPELLENT COMPOSITIONS CONTAINING AROMATIC ALDEHYDES

[75] Inventors: Ralph W. Emerson; Bradford G. Crandall, Jr., both of Davis, Calif.

[73] Assignee: Proguard, Inc., Suisun City, Calif.

[21] Appl. No.: 778,061

[22] Filed: Dec. 24, 1996

Related U.S. Application Data

[63] Continuation-in-part of Ser. No. 640,962, May 9, 1996, which is a continuation-in-part of Ser. No. 486,943, Jun. 7, 1995.

[51] Int. Cl.$^6$ .................................................. A01N 25/22
[52] U.S. Cl. .......................... 424/405; 424/403; 424/406; 514/919; 514/701
[58] Field of Search .......................... 424/403, 405–407; 514/916, 919, 701

[56] References Cited

U.S. PATENT DOCUMENTS

| | | | |
|---|---|---|---|
| 4,477,361 | 10/1984 | Sperti et al. | 252/106 |
| 4,943,674 | 7/1990 | Houck et al. | 800/205 |
| 4,978,686 | 12/1990 | Sotome | 514/698 |
| 5,093,326 | 3/1992 | Herman | 514/172 |
| 5,166,317 | 11/1992 | Wallace et al. | 530/350 |
| 5,175,095 | 12/1992 | Martineau et al. | 435/69.1 |
| 5,177,011 | 1/1993 | Shewmaker et al. | 435/172.3 |
| 5,196,200 | 3/1993 | Wilson | 424/411 |
| 5,202,247 | 4/1993 | Kilburn et al. | 435/195 |
| 5,315,001 | 5/1994 | Krindl et al. | 536/23.6 |
| 5,340,731 | 8/1994 | Kilburn et al. | 435/179 |
| 5,536,501 | 7/1996 | Emerson et al. | 514/699 |

FOREIGN PATENT DOCUMENTS

| | | |
|---|---|---|
| 9203533 | 3/1994 | Brazil . |
| 2529755 | 1/1984 | France . |
| 3605753 | 8/1987 | Germany . |
| 57-040402 | 3/1982 | Japan . |
| 57-126401 | 8/1982 | Japan . |
| 0051797 | 3/1985 | Japan . |
| 3228083 | 9/1988 | Japan . |
| 1261303 | 10/1989 | Japan . |
| 3007554 | 1/1991 | Japan . |
| 3010632 | 1/1991 | Japan . |
| 3127702 | 5/1991 | Japan . |
| 3268901 | 11/1991 | Japan . |
| 428803 | 1/1992 | Japan . |
| 4149103 | 5/1992 | Japan . |
| 4176460 | 6/1992 | Japan . |
| 4117125 | 5/1993 | Japan . |
| 5139924 | 6/1993 | Japan . |
| 5178712 | 7/1993 | Japan . |
| 6041576 | 2/1994 | Japan . |
| 8239700 | 9/1996 | Japan . |
| 8900902 | 5/1989 | Sweden . |
| WO93/05159 | 3/1993 | WIPO . |
| WO93/24638 | 12/1993 | WIPO . |
| WO94/08036 | 4/1994 | WIPO . |
| WO94/24158 | 10/1994 | WIPO . |

OTHER PUBLICATIONS

Bowles and Miller, *J. Food Protection* (1993) 56: 788–794.
Casey and Dobb, *Enzyme Microb. Technol.* (1992) 14: 739–747.
Cowles et al., *Cinnamyl derivatives and monoterpenoids as nonspecific ovipositional deterrents of the onion fly.* (1990) 16: 2401–2428.
Frear, *Chemistry of Insecticides and Fugicides* (1942) 13: 184–191.
King, *Agriculture Handbook.* (1954) 69: 1–397 (relevant pages attached).
Reifenrath et al., *J. Am. Mosquito Control* (1989) 5: 45–51.
Yuan et al., *Fundamental & Applied Toxicol.* (1993) 20: 83–87.

*Primary Examiner*—Daniel S. Levy
*Attorney, Agent, or Firm*—Viola T. Kung; Barbara Rae-Venter; Rae-Venter Law Group,P.C.

[57] ABSTRACT

Repellent compositions which contain aromatic aldehydes such as cinnamic aldehyde, α-hexyl cinnamic aldehyde and/or coniferyl aldehyde are provided, together with methods for their use as repellents for pests including flies, cockroaches, aphids, silverleaf white flies, mosquitoes, ticks, fleas, lice, leafhoppers, thrips, two-spotted spider mites, snails, slugs, biting midges, earwigs, and moths. Also provided are stabilized α-hexylcinnamic aldehyde (HCA) compositions which reduce the evaporation rate of HCA and/or induce HCA to evaporate at a constant rate over time.

12 Claims, 8 Drawing Sheets

REPELLENT COMPOSITIONS CONTAINING AROMATIC ALDEHYDES

CROSS-REFERENCE TO RELATED APPLICATIONS

This application is a continuation-in-part of U.S. Ser. No. 08/640,962, pending filed May 9, 1996, which is a continuation-in-part of U.S. Ser. No. 08/486,943, pending filed Jun. 7, 1995, which disclosures are incorporated herein by reference.

INTRODUCTION

1. Technical Field

This invention relates to aromatic aldehydes as pest repellents. The invention provides stabilized compositions of α-hexyl cinnamic aldehyde (HCA) which reduce the evaporation rate of HCA and/or induce HCA to evaporate at a constant rate over time. The invention is exemplified by the use of cinnamic aldehyde or HCA for repelling animal pests such as mosquitoes, fleas and chiggers, and for, repelling agricultural pests such as aphids and thrips. The stabilized HCA compositions are exemplified by the use of one or more polymers including polyvinyl pyrrolidone/eicosene copolymer, hydrated silica, dimethione and mineral oil.

2. Background

In many countries today, diseases such as malaria, vector-borne hemorrhagic fevers, cockroaches, allergies, filth, fleas, bubonic plague, ticks, viruses, rickettsiae, spirochetes, bacteria, snails, schistosomiasis, and sand fly fever are still responsible for serious illnesses and numerous deaths among inhabitants. The ever-growing concern for the protection of endangered species and the downward trend in availability of broad spectrum pesticides due to public health concerns are forcing scientists to look for other economical means of providing protection from diseases spread by pest-borne vectors. Moreover, the cost of pesticides often is too high for many of the less developed nations and the increasing resistance to pesticides by vector populations is a growing problem.

Diseases spread by vectors also affect plants. Insect infestations of trees and other woody plants destroy millions of ornamental and agricultural trees every year. For example, Dutch Elm Disease has destroyed millions of elm trees across the United States. The disease is caused by a fungus which is spread from tree to tree by a particular species of insects attracted to the elms. Current treatments for plant diseases are only partially successful, and may render a crop of agricultural products worthless due to their persistent toxicity.

The use of repellents is an excellent alternate means of providing relief when other conventional vector control methods are not feasible or are ineffective. For animal vector targets, repellents properly applied to the skin and/or clothing are an inexpensive and practical means of reducing the biting activity of hematophagous arthropods and for the prevention of disease transmission by vectors: repellents are effective against a wide range of disease-carrying vectors.

This is in comparison to, for example vaccines, where a separate vaccine must be developed for each disease. Moreover, only a few vaccines are effective against vector-borne diseases.

Detractions from the use of repellents in vector control and disease prevention usually center on questions of safety and cost. For example, one of the more extensively used repellents was the 6-2-2 repellent which contained dimethyl phthalate, ethyl hexanediol, and indalone in the proportion 6:2:2. Dimethyl phthalate and indalone are still in limited use, but in 1991, the U.S. Environmental Protection Agency canceled all registrations of ethyl hexanediol at the request of the manufacturers concerned. This action was taken because of new information on possible adverse effects of the compound on fetal development.

Another example, of a questionably safe repellent is DEET (N,N-diethyl-1,3-methylbenzamide). This material virtually eclipsed other repellents for topical use, and it remains the principal repellent in use today, nearly 40 years after its discovery. DEET is a profound dermal penetrant, it penetrates skin. As a repellent, DEET is highly effective, but it smells bad and leaves a greasy feeling on the skin; in addition, it can cause allergic and toxic effects, especially when used repeatedly on the skin in high concentrations. Repellent formulations containing 90-99% DEET are considered high concentrations, whereas repellent formulations containing 50% or less DEET are considered as effective as a concentration of 100%. A concentration of 33% DEET is effective in providing 10-14 hours of protection. For products containing even low concentrations of DEET, however, it is recommended that the skin be cleaned with mild soap and rinsed with water as soon as the repellent is no longer needed, in order to minimize possible adverse reactions. These recommendations frequently are impractical in third world countries and for military use. Since its implementation for use as a mosquito repellent in the mid-1950's, extensive efforts have been made to improve DEET's performance. DEET must remain on the skin surface to be an effective repellent. By limiting excessive evaporation and reducing loss due to skin penetration, a lower concentration of DEET will maintain efficacy and improve user acceptability (i.e., smell and feel). However, DEET plasticizes the very polymers that could enhance its performance. In spite of extensive efforts, to date, a user acceptable formulation of DEET to control the repellent's reservoir on the skin surface has not been developed.

Repellent compositions are available for repelling insects from agricultural crops, for topical application to animals, as well as for repelling insects from entering a dwelling or other area. However, the safety of many of the topical compositions has been questioned. Moreover, many of the topical compositions are of limited effectiveness, especially in areas of severe infestation with insects. Treatment for external insect infestations of a mammal, such as lice or crabs, involves topical application of often harsh toxic insecticidal compositions to skin or scalp. Irritation often develops, and adverse health effects from long-term use also are known. Repellent compositions for the prevention of entry of insects into an area are similarly ineffective. In addition, many of the known repellent compositions are not safe for use in enclosed spaces due to their high toxicity, especially where children and pets may come into contact with them. Moreover, many of the known repellent compositions damage the plants, such as foliar surfaces and flowers. A need therefore exists for a non-irritating, non-toxic, effective repellent composition. A need also exists for a relatively non-persistent, non-phytotoxic and effective means for repelling insect infestations of trees and woody shrubs. By non-persistent is intended that the composition unless prepared as a long-lasting formulation does not remain on the treated surface.

Relevant Literature

U.S. Pat. No. 5,093,326 discloses repellent compositions which include an ozonized unsaturated hydrocarbon, includ-

3 ing terpenes. U.S. Pat. No. 5,365,017 discloses preparation of a transgenic plant having increased levels of cycloarterol. Publications relating to repellent formulations include Reifenrath et al. (1989) *J. Am. Mosquito Control Association* 5: 45–61 and Reifenrath (1995) *Cosmetics & Toiletries Magazine* 110: 85–93, SE 8900902, BR 9203522, JP 57126401, JP 3127702, JP 1261303, JP 5178712, JP 3268901, JP 3007554, JP 57040402, *J. Chem. Ecol.* (1990) 16:8: 2401–2428, DE 3605753, JP 5139924, JP 4176460, FR 2529755, JP 57120501, a JP 1261303.

SUMMARY OF THE INVENTION

The present invention provides repellent compositions which contain aromatic aldehydes and methods of using these compositions. The repellent compositions contain a compound which has a formula shown in (1) below:

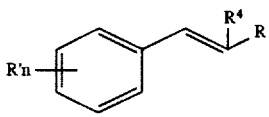

wherein R represents —CH$_2$OH or —CHO; n is an integer from 0 to 3; and each R' independently represents OH or an organic substituent containing from 1 to 10 carbon atoms and from 0 to 5 heteroatoms, wherein the total number of carbon and heteroatoms in all R' substituents of said compound is no more than 15; and R$^4$ represents hydrogen or an organic constituent containing from 1 to 10 carbon atoms. These compounds include natural compounds, such as cinnamic aldehyde. Also of interest are α-substituted aldehydes, such as α-hexyl cinnamic aldehyde (HCA). In use, the compounds are applied to a surface, such as skin, clothing, bark, plant parts, habitat components and the like, from which it is desirable to repel insects and other pests. In addition, the combination of HCA with one or more stabilizing agent alters the evaporation rate of the composition to approximate the minimal effective evaporation rate (MEER) necessary to repel pests. A preferred HCA formulation has an evaporation rate that exceeds and approximates the MEER necessary to repel a pest and is constant over time. The invention finds use, for example, in the prevention of disease and infection which can result from contact between a host animal or plant and a disease-carrying insect vector or other pest vector.

DESCRIPTION OF SPECIFIC EMBODIMENTS

Figure 1:
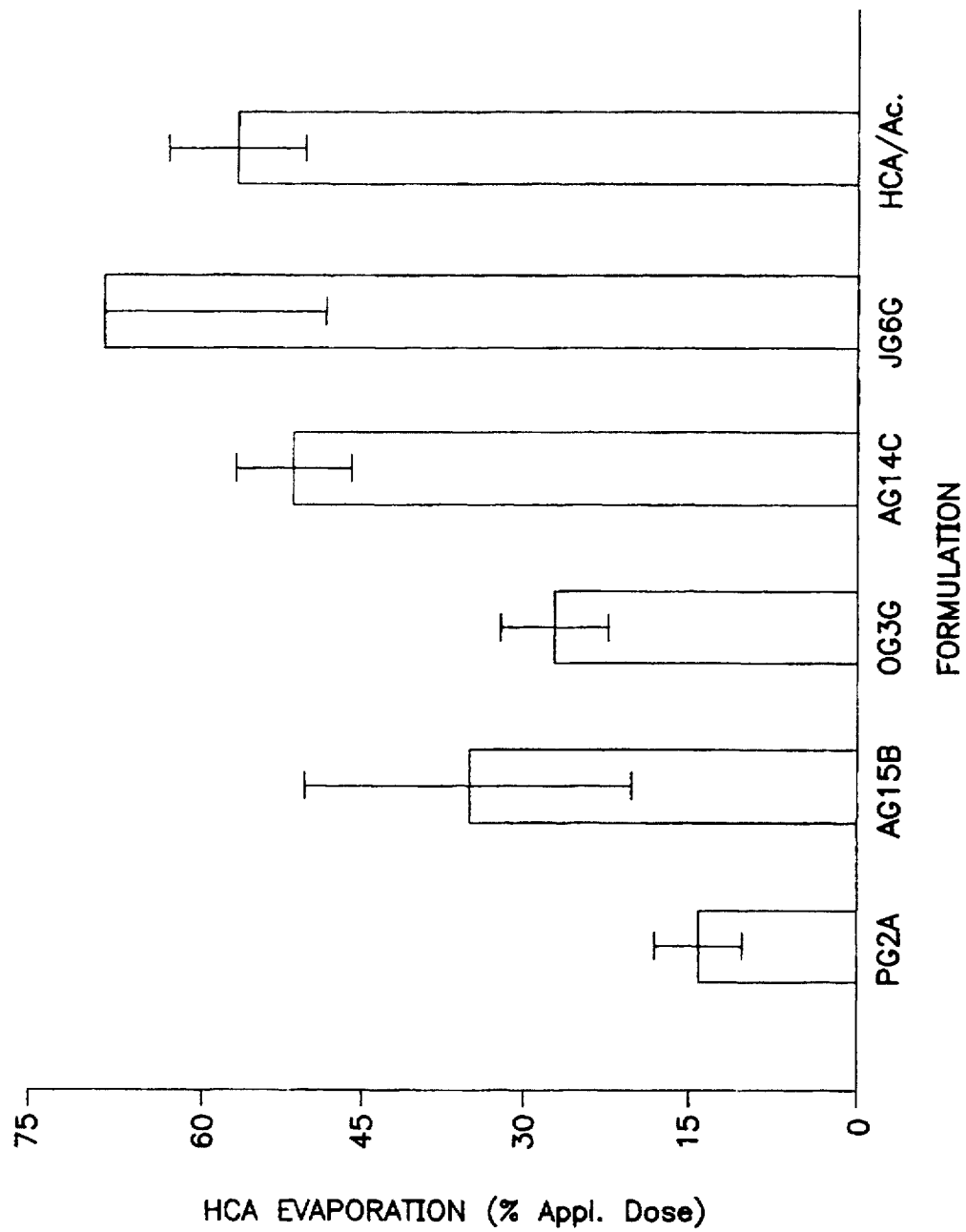
FIG. 1 shows total HCA evaporation of the 5 stabilized HCA compositions and the control HCA composition.

Methods and compositions are provided for obtaining and/or maintaining an area substantially free of insects and other pests. Mammals, birds, fish and their habitats, as well as seeds, seedlings, plants, and plant parts such as fruit substantially free of pathogenic organisms such as fungi, insects and other pests, as well as viruses, bacteria, spirochetes, and other disease-causing organisms, and sap-sucking insects are provided. Also provided is a method to repel pests and disease-causing organisms. A surface of interest is contacted with a formulation comprising one or more aromatic aldehyde(s) in an amount sufficient to provide an aroma to repel an insect or other pest. The amount of repellent that is applied depends in part upon the nature of the surface, and to some extent upon the formulation and the specific compounding use and, therefore, is empirically determined for best results with a particular insect or other pest.

The compositions and methods of the subject invention offer several advantages over existing compositions and methods. A major advantage is that the formula components are generally regarded as safe (GRAS) and are approved for food use. For example, a number of the aromatic aldehydes which find use in the subject invention, such as α-hexyl cinnamic aldehyde (HCA), cinnamaldehyde, and vanillin are GRAS synthetic flavoring agents (21 CFR §172.515). HCA was in public use before the 1950's and today is widely used in consumer preparations such as soaps, detergents, creams, lotions, and perfumes. (Monographs on fragrances raw materials. *Food Cosmet. Toxicol.* 12: suppl., 915, 1974). HCA was granted GRAS status by the Flavoring Extract Manufacturers'Association (FEMA) in 1965 and is approved by the US FDA for use in food (21CFR121.1164). (Survey of flavoring ingredient usage levels No.2569. Fd. Technol., Champaign, 19: (part 2)155, 1965). The Council of Europe (1970) included HCA in the list of admissible artificial flavoring substances at a level of 1 ppm. (Council of Europe. Natural and Artificial Flavouring Substances. Partial Agreement in the Social and Public Health Field. Strasbourg, List A(1), Series 1, no. 129, p. 55, 1970).

An additional advantage is that when applied to animals, including humans, the subject formulations are non-toxic and non-irritating to the skin, and have long-lasting repellent effects. For example, α-hexyl cinnamaldehyde (HCA) has an oral LD$_{50}$ of 3.1 g/kg in rats and a dermal LD$_{50}$ of greater than 3 g/kg (Moreno, O.M. Report to RIFM, Mar. 24, 1971). HCA was found to be moderately irritating when the neat compound was applied to intact or abraded rabbit skin for 24 hours under occlusion (Moreno). When tested at 12% in petrolatum, HCA produced no irritation after a 48 hour closed-patch test on human subjects and produced no sensitization in a maximization test carried out on 25 human subjects (Kligman (1966) *J. Invest. Dermatol.* 47:393). HCA at 20% in diethylphthalate produced no positive reactions in a repeated insult patch test conducted on 100 human subjects. Jimbo (1983) *J Dermatol.* 10:229–239 tabulated allergenicity data found in the literature for 18 fragrance compounds. While cinnamic aldehyde had a positive reaction from the human maximization test, HCA was negative in the test. Patch test results of 2% HCA on 100 eczema and dermatitis patients were negative (0 positive results out of 100). Of 4 patients sensitive to 2% cinnamaldehyde, none were found to be sensitive with 2% HCA. The skin sensitization frequently reported for cinnamaldehyde is probably initiated by reaction of the aldehyde fimctional group with amino groups on proteins. Substitution of bulky alkyl groups in the alpha position (e.g. the hexyl group of HCA) relative to the aldehyde group can reduce this reactivity by creating steric hindrance as well as reducing the electrophilicity of the aldehydic carbon. Alpha-substituted cinnamaldehydes, to which skin sensitization is uncommon, react very slowly or not at all with amines in comparison with cinnamaldehyde. In studies using the maximization test in guinea pigs, Senma and coworkers (1978) *Acta Derm Venered*

(Stockholm) 56:121–124 reported a tendency that, as the number of hydrocarbons of alkyl groups replacing the alpha-hydrogen in cinnamaldehyde increased, the rate of sensitization reaction declined. The use of these compositions in an agricultural setting in place of currently used pesticides therefore decreases the likelihood of adverse side effects to field workers, or to animals, fish or fowl which ingest the tissues or parts of plants which have been treated or come into contact with treated soil. In addition, the subject invention overcomes the failure of current pesticides to translocate, for example, to roots for repelling root-dwelling pests such as phylloxera. Prevention of infestation by repelling the vector which carries diseases, or damages the target for the pest, significantly decreases the number of target animals or plants which will succumb to disease carried by the pest or be damaged by the activities of the pest. An example is the damage done by female medflies as they oviposit on fruit. Decreasing pest infestation generally results in healthier plants or animals and better quality and/or quantity of crops or other products. The aromatic aldehydes have positive organoleptic and olefactory properties which in some cases can improve the flavor and/or smell of treated surfaces and eliminate the unpleasant odor associated with many pest repellents. The odor of α-hexyl cinnamic aldehyde (HCA), for example, is described as floral or jasmine-like with some herbaceous character.

Another advantage is that the surfactants which are used as emulsifiers in the subject formulations, such as the Tweens (polysorbates) are already used as food additives, and saponin also has GRAS status. In addition, formulation residuality can be managed. This is of great benefit for integrated pest management programs with beneficial insects and/or microorganisms such as yeast, fungi and bacteria because short term residuals can be obtained. For other applications where long term effects are desired, residuality can be increased by the use of polymer formulations. As an example, the reduction of HCA evaporation using various polymer formulations decreases excessive evaporation following topical application of a formulation, thereby extending the duration of efficacy and reducing odor perception to improve user acceptability. The stabilized formulation preferably increases the amount of HCA remaining on a skin surface and decreases mean cellular penetration of skin into epidermis or dermis. The low penetration of HCA into epidermis and dermis minimizes possible side effect of HCA. These formulations are effective and have a long-lasting effect to repel pests, for example, from keratineous surfaces such as mammal skins, and from porous and non-porous surfaces such as fiber, glass, wood, paper, cellulose and cloths. Other advantages include the repellent effects of the compositions on some animals, including predatory animals such as coyotes. See U.S. Pat. No. 4,097,607. Use of the formulation to kill insect pests on animals such as sheep, therefore, has the additional advantage that animals which prey on the sheep also are repelled. Birds such as pigeons and starlings are repelled offering additional protection to agricultural products such as fruit and seed. See U.S. Pat. No. 4,097,607.

The subject formulations also provide for effective repulsion of multiple organisms, such as both fungi and insects. This multi-target efficacy reduces the need for application of multiple agents to a plant or animal to be protected, and substantially eliminates the need for application of pesticides. In particular situations, such as where an insect damages an animal or a plant part or tissue and a secondary fungal or bacterial disease develops, this aspect of the invention is particularly advantageous.

The general formulation is as shown in formula (1) above. A preferred formulation is shown in formula (2) below:

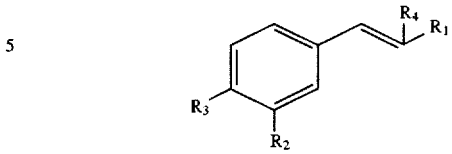

wherein $R_1$ represents —CHO, $R_2$ represents —H, a methoxy group, or organic substituent containing from 1 to 10 carbon atoms, $R_3$ represents —H, —OH, or an organic substituent containing from 1 to 10 carbon atoms, and $R_4$ represents a hydrogen or an organic substituent containing from 1 to 10 carbon atoms. Examples of aromatic aldehydes of use in the present invention are cinnamic aldehyde ((3) below):

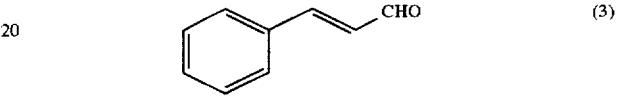

and coniferyl aldehyde ((4) below):

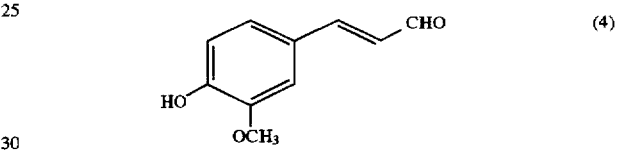

Other compounds of interest include analogs of the compound of formula (1) such as compounds substituted at the alpha postion with an alkyl, such as a hexyl group, or a branched alkyl group such as an amyl group. Generally the group at the alpha position is from C-5 to C-C-10. Such compounds include α-hexyl cinnamaldehyde and α-amyl cinnamaldehyde. The chemical structure of α-hexyl cinnamic aldehyde (HCA) is shown in (5) below.

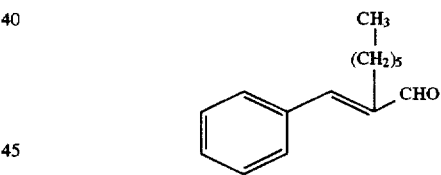

The Chemical Abstracts Service (CAS) name of HCA is 2-(phenylmethylene) octanal and the CAS Registry Number is (101-86-0). The compound also is described by the chemical name of 3-hexyl-3-phenyl-2-propenal. The compound's formula is $C_{15}H_{20}O$ and the molecular weight is 216.3. HCA can be obtained from Firmenich; their product is composed principally of the (E)-cis isomer (93.8% maximum), and the (Z)-trans isomer (6% maximum). Among minor components is the self aldol condensation product of octanal (1–1.5%).

The aromatic and aliphatic aldehydes of the subject invention can be prepared by various synthetic methods known to those skilled in the art. For example, see, J. March, ed., Appendix B.*Advanced Organic Chemistry: Reactions, Mechanisms, and Structure*, 2nd Ed., McGraw-Hill, New York, 1977. Cinnamaldehyde can be prepared synthetically, for example, by oxidation of cinnamyl alcohol (Traynelis et al., *J Am. Chem.* Soc. (1964) 86:298) or by condensation of styrene with formylmethylaniline (Brit. patent 504,125). The subject aldehydes also can be obtained by isolation from natural sources. For example, cinnamaldehyde can be isolated from the woodrotting fungus *Stereum subpileatum* (Birkinshaw et al., *Biochem. J.* (1957) 66:188), and α-hexyl cinnamic aldehyde (HCA) can be obtained from rice, or synthesized as described in U.S. Pat. No. 5,055,621.

In a preferred embodiment, the formulation includes α-hexyl cinnamic aldehyde, cinnamic aldehyde and/or coniferyl aldehyde in a formulation containing Tween 80 or saponin as an emulsifier and may include sodium bicarbonate. The preferred formulation for repelling flies, mosquitoes, fleas, lice, cockroaches, two-spotted spider mites, silverleaf white flies, aphids, leafhoppers, thrips and ants is 10–5000 ppm of aromatic aldehyde; for ticks, 100–2500 ppm of aromatic aldehyde. Generally, the total amount of aromatic aldehyde(s) present in the formulation is 2% or less. Due to minimal skin sensitization by α-hexyl cinnamic aldehyde, up to 20% of (α-hexyl cinnamic aldehyde can be included in a formulation for skin application; higher amounts can be used for application to non-living surfaces in areas which will not come into contact with a living surface. The formulations are effective without the use of antioxidants; particular aldehydes have inherent antioxidant properties, for example, coniferyl aldehyde. Alcohols, such as glycols, including propylene glycol and polypropylene glycol, are likewise not required for efficacy of the formulations and in fact can be harmful where the application is to a plant and are preferably omitted from formulations for agricultural use. Formulations of particular interest include HCA and stabilizing agents. The stabilizing agents decrease the evaporation rate of HCA from a surface and decrease the HCA penetration for example into skin. The stabilizing agents also increase the physical and chemical stability of the HCA-containing formulation.

The effective amount for repelling particular pests, for compositions including compounds of formula (3) and/or formula (4) and/or formula (5) as well as the amount of other compounds of formula (1) which find use, can be determined using protocols known to those of skill in the art for evaluating repellent efficacy of compounds. Examples of such protocols follow. These protocols also can be used to optimize each formulation for specific pathogens using any of the compounds encompassed by formula (1) or formula (5) as well as for specific applications to minimize plant phytotoxicity or skin sensitivity and other side effects for animals while maximizing the repellent effect of the formulation.

Although the aromatic aldehydes can be formulated alone, they can be used in combination with other active or inactive substances. As an example, the aromatic aldehyde (s) can be rendered substantive by including an emulsifier such as Tween 80. Other detergents which can be used include anionic detergents such as those described in U.S. Pat. No. 4,978,686. Generally, detergents and other agents used in the formulation do not detract from the repellent properties of the aromatic aldehydes but do increase the substantive properties of the formulation (see for example, U.S. Pat. No. 4,477,361) and may improve the repellent properties. Additional components such as an aqueous preparation of a salt of a polyprotic acid such as sodium bicarbonate, sodium sulfate, sodium phosphate or sodium biphosphate can be included in the formulation, to increase the antifungal properties of the formulation. Calcium salts also can be used. The resulting emulsion is diluted to an appropriate concentration before use.

In some instances, the efficacy of the formulation can be increased by adding one or more other components, i.e., a compound other than a compound of formula (1) or (5), to the formulation when it is desirable to alter particular aspects of the formulation. As an example, it may be desirable for certain plant applications if there is an undesirable amount of phytotoxicity with a particular formulation to decrease the phytotoxicity effect (phytotoxicity rating of 2 or less, with 1 or less preferred, see below) or it may be necessary to increase the repellent effect of the formulation, or both. It is preferable that the additional component(s) minimize any side effects to plants or animals while increasing the repellent effect of the formulation.

Of particular interest is the use of a component(s) which is a synergist to increase repellency while minimizing any side effects as related to a particular formulation. By "synergist" is intended a component which, by virtue of its presence, increases the desired effect by more than an additive amount. The concentration of one or more of the other formulation ingredients can be modified while preserving or enhancing the desired repellent effect of the formulation. Particularly desirable is the addition of components to a formulation to allow for a reduction in the concentration of one or more other ingredients in a given formulation while substantially maintaining the efficacy of the formulation. Combination of such a component with other ingredients of the formulation can be accomplished in one or more steps at any suitable stage of mixing and/or application of the composition. The effective amount of synergist used can be determined by means known to those of skill in the art.

Preferred additional components also include saponins, as they can be substituted for surfactants as emulsifying agents, and additionally, on at least same plants, have a growth promotant effect at the concentrations used and/or increase the glossiness of the leaves and/or fruit. Generally, the use of saponin does not interfere with the repellent properties of the formulation. Saponins are a class of compounds, each containing a sapogenin portion and a sugar moiety. The sapogenin may be a: steroid or a triterpene and the sugar moiety may be glucose, galactose, a pentose, or a methylpentose. S. Budavari, ed., *The Merck Index*, 11th ed., Merck & Co., Inc., Rahway, N.J., 1990, p. 1328. The saponins for use in the present invention can be produced and/or isolated from various plant parts including fruit, leaf, seed and/or root, using means known in the art, from a variety of sources including the various plants known to produce them, ranging from yucca, quillaja, agave, tobacco, licorice, soybean, ginseng and asparagus to aloe woods. Saponins for use with the present invention are preferably non-toxic to humans and higher animals. Most preferably the saponin for use in the present invention is non-toxic food grade, the source being from yucca plants. Even more preferred are the saponins from Yucca schidigera or Y valida and their equivalents. The saponins are generally prepared by a cold press extraction process and the resulting liquid extract used. The yucca fiber also can be used; it is typically sundried, mulled and sized by screening.

A variety of structurally related saponins are known, the most variable structural feature being the glycosylation pattern. S. Budavari, ed., *The Merck Index*, 11th ed., Merck & Co., Inc., Rahway, N.J., 1990, p. 1328. Saponins also may contain additional modifications, such as sarasaponins which are saponins with a steroid attached, and saponin structure can be modified by any number of enzymatic, chemical and/or mechanical means known in the art. Saponins from Yucca schidigera contain steroidal saponins with the major sapogenins being sarasapogenin and tigogenin. The sarasaponin yields on hydrolysis, sarasaspogenin (sarasaspogenin 5-beta, 20-betaF betaF, 22-deltaF, 25-betaF;

also known as spirostan-3-beta-01 and parigenin), glucose and galactose. The saraspogenin has a molecular formula of $C_{27}H_{44}O_3$. Nobel, Park S., Agaves, Oxford Univ. Press, New York, 1994. An effective amount of saponin is of the range of about 0.01 to 3% generally in the range 0.01 to 0.1% and most preferably about 0.25% v/v aqueous solution of $10°$ brix saponin extract. $10°$ brix is a term of art in sugar chemistry. The brix degree equals the percent by weight of sugar in the solution. Hawley, ed., *The Condensed Chemical Dictionary*, 10th ed., Van Nostrand Reinhold, New York, 1981, p. 149.

In addition to the specific compounds of the formulas (1), (2), (3), (4) and (5) above, precursors of any of these compounds that produce a compound of the formulas identified above upon action of a biological system on the precursors are considered to be equivalent to compounds of the invention. Thus application of precursor compounds to plant parts or tissues would be equivalent to the practice of the present invention. Biological conversion of precursor compounds into aromatic aldehydes is described in, for example, U.S. patent application Ser. No. 5,149,715 and references cited therein. See also Casey and Dobb *Enzyme Microb. Technol.* (1992) 14: 739-747.

The method of the present invention is carried out by introducing to a surface of interest a sufficient amount of a repellent agent to repel the insect or other pest. By repelling a disease carrying vector at 100% repellency, the disease is prevented. For example, malaria is prevented if the disease carrying vector mosquito is repelled from a mammal's body. Where the surface of interest is skin, fur, hair, clothing and the like, the application can be by way of contacting the surface of interest with a formulation that has been rendered substantive (see, for example, U.S. Pat. No. 4,477,361) for the surface of interest so that a repellent amount of the formulation remains on the surface so treated and is released at a rate sufficient to repel a susceptible insect or other pest. A formulation containing the repellent agent generally is introduced by topical application to a surface. For example, the formulation is sprayed on, as a wet or dry formulation, the top and/or underside as applicable to the surface of interest. Among the formulations suitable for application are sprays, sticks, and repellent oils or ointments (see, for example, U.S. Pat. No. 4,978,686 and Japanese Patent No. 1261303). In some instances, the surface of interest can be impregnated with the repellent formulation by absorption into the surface. Alternately, the formulation can be applied wet or dry to the rhizosphere where it can vaporize in the vicinity of the roots and associated pathogenic organisms which colonize the roots at a rate sufficient to repel a susceptible insect or pest. In some instances, air can be introduced into the rhizosphere to increase the vaporization process. To prevent an ingress of insects into an area, the compositions of the invention can be applied to surfaces within and/or surrounding the area, for example, the compositions can be applied to doors, windows and other openings of a building and/or to surfaces that surround these openings.

Where the surface of interest is a plant or plant part, the presence of the repellent agent can be as a result of topical application; for example, the compositions can be aerially applied to crops, or it can be by elaboration from the host plant as a result of genetic modification of the host plant. In the latter case, a plant host expressing a gene encoding an enzyme required to control the level of the compound of interest results in the exposure of a target organism to at least one component of the repellent formulation. At least one component of the repellent formulation can be expressed by the plant host and optionally other components of the repellent formulation are exogenously applied to the plant host so that the combination elicits the desired repellent effect. Transgenic plants (see for example, U.S. Pat. Nos. 4,943,674 and 5,175,095) having an increased ability to accumulate aromatic aldehydes such as cinnamaldehyde and coniferyl aldehyde and HCA to provide self-protection against plant pests or to be used as a natural source of aromatic aldehydes for extraction and subsequent use as a repellent can be prepared.

The methods involve transforming a plant cell of interest with an expression cassette functional in a plant cell comprising as operably linked components in the 5' to 3' direction of transcription, a transcriptional and translational initiation regulatory region, joined in reading frame 5' to a DNA sequence encoding and capable of modulating the production and/or required to produce the compound of interest, and translational and transcriptional termination regions. Expression of an enzyme required to produce the compound of interest provides for an increase in production of the compound as a result of altered concentrations of the enzymes involved in the compounds' biosynthesis. Of particular interest is the selective control of cinnamic and/or coniferyl aldehyde and/or HCA production in plant tissues such as leaves, roots, fruits and seeds. One or more compounds of the present formulations can be produced by modulating the expression of one or more genes or a gene encoding one or more enzymes or an enzyme pathway or cluster required to control the level of the compound of interest in a plant, plant part, plant cell, specific plant tissue and/or associated with a particular stage of plant growth.

The enzyme or enzymes can be in a biosynthetic pathway or a degradation pathway and the regulation will be up or down respectively; i.e., to modulate expression of an indigenous or an endogenous plant gene. An indigenous plant gene is one which is native to the genome of the host plant. An endogenous plant gene is one that is present in the genome of the plant host of interest, and may be an indigenous gene or a gene that is present as a result of infection of the plant (e.g., a viral gene), or otherwise naturally incorporated into the plant genome. The host plant also can be modified by recombinant means or by traditional plant breeding methods to introduce one or more genes exogenous to the host plant which encode enzymes which control the level of the compound of interest and/or are in the synthetic pathway for one or more compounds of formula (1), (2), (3), (4) or (5). By "modulation of gene expression" is intended control of production of a gene product of interest at the level of transcription, translation and/or post translation. The level of the compound of interest is controlled by modulating the expression of one or more endogenous genes or transgenes encoding one or more enzymes required to synthesize the compound of interest.

Accumulation of aromatic aldehydes can be achieved by downregulating the expression of specific plant genes that encode enzymes which either cause further metabolism of the desired aldehydes or divert metabolic intermediates away from the desired aldehydes. In the case of cinnamaldehyde, for example, this involves downregulating the expression of cinnamate 4-hydroxylase (CA4H) and cinnamic alcohol dehydrogenase (CAD). CA4H ordinarily diverts some cinnamic acid away from cinnamaldehyde to produce p-coumaric acid, itself a metabolic intermediate. Reducing CA4H activity alone is not sufficient to cause accumulation of cinnamaldehyde because CAD can rapidly convert cinnamaldehyde to cinnamyl alcohol, which then becomes incorporated into lignin or accumulates as glycosides. Simultaneously reducing both CA4H and CAD activities results in increased metabolic flux from cinnamic acid into cinnamaldehyde and decreased conversion of cinnamaldehyde into cinnamyl alcohol. Some cinnamaldehyde becomes incorporated into lignin but cinnamaldehyde (either free or as glycosides) also accumulates to above-normal levels, particularly at times when the biosynthesis of cinnamic acid is elevated. This occurs when the level of phenylalanine ammonia lyase (PAL; the first and rate-limiting step in general phenylpropanoid metabolism, Hahlbrock and Scheel (1989) *Annu. Rev. Plant Physiol. Plant Mol. Biol.* 40:347–369) activity is high, a situation that naturally occurs in plants in response to a wide range of stimuli including invasion by fingal pathogens and mechanical damage associated with wounding and insect feeding.

Inhibiting CAD activity in transgenic plants has been proposed as a method of reducing lignin synthesis in plants and thereby improving the digestibility of fodder crops (WO 93/05159). These experiments suggested that lignin biosynthesis had been altered qualitatively, but not necessarily quantitatively, but did not demonstrate or appreciate the desirability of accumulating cinnamaldehyde as a method of increasing insect and other pest repellancy. A number of plant CA4H and CAD genes have been cloned and their sequences are available from GenBank. Portions of these genes that include nucleotide sequences that are conserved between different plant species can be used directly in a plant expression vector (antisense or sense orientation) to suppress the expression of the corresponding endogenous genes (e.g., Pear, et aL, *The Plant Cell Antisense Res. and Develop.* (1993) 3:181–190, Napoli, et al., *The Plant Cell* (1990) 2:279–289). More preferably, these conserved gene sequences are used to isolate CA4H and CAD cDNA clones from a cDNA library of the plant species that is to be modified. The resulting cDNA clones, or portions thereof which encode a desired enzyme activity, are then introduced into a plant expression vector (antisense or sense) and used to transform the plant(s) of interest. DNA constructs according to the invention preferably comprise a sequence of at least 50 bases which is homologous to the endogenous CA4H or CAD genes.

Methods for modulating gene expression in plants are known in the art. Variation in growth conditions or exogenous application of compounds to a plant can affect gene expression. At the molecular level, gene expression depends substantially on the transcription, translation and termination control regions which regulate expression of a structural gene coding region. By exploiting the plant signals which regulate these control regions or by the direct recombinant manipulation of the control regions, expression of a gene encoding an enzyme required to control the level of cinnamic aldehyde, for example, can be modulated. When a transgene is supplied exogenously to a plant host, the transgene includes control regions that are selected and designed to achieve the desired tissue and/or level and timing of gene expression. As appropriate, the control regions can be homologous (native) or non-homologous (non-native) to the gene of interest. By "homologous" is meant that the control region(s) is from or substantially similar to a control region normally associated with the gene of interest. By "non-homologous" is meant that the control region(s) originates from a different nucleotide source or sequence or is substantially different from the control region(s) normally associated with the gene of interest. For example, if the enzyme coding sequence is non-homologous in source as compared to the control regions, in order to have expression of the gene in a plant cell of interest, transcriptional and translational initiation regulatory regions or promoters functional in the plant cell are provided operably linked to the coding sequence.

Transcription and translation initiation signals functional in plant cells include those from genes which are present in the plant host or other plant species, and direct constitutive or selective expression in the plant host. A common promoter that is used to provide strong constitutive expression of an introduced gene is the cauliflower mosaic virus (CaMV) 35 S promoter (available from Pharmacia. Piscataway, N.J.). Either constitutive promoters (such as CaMV 35S) or inducible or developmentally regulated promoters (such as the promoter from a PAL gene or the endogenous CA4H or CAD genes) can be used. Use of a constitutive promoter tends to affect finctions in all parts of the plant, while use of an inducible or developmentally regulated promoter has the advantage that the antisense or sense RNA is only produced in the tissue and under the conditions it is required. The use of developmentally regulated promoters is preferred in the use of this invention because it is known that down-regulation of phenylpropanoid biosynthesis can produce undesirable side-effects on the development of transgenic plants containing a heterologous PAL gene (Elkind, Y. et al., *Proc. Nat. Acad. Sci.* (1990) 87:9057–9061).

For selective control of biosynthesis of aromatic aldehydes such as cinhnamic and/or coniferyl aldehyde and/or HCA in a plant tissue of interest, plant cells are transformed with an expression cassette comprising DNA encoding a structural gene for one or more enzymes required to synthesize cinnamic and/or coniferyl aldehyde and/or HCA and capable of increasing the amount of these aldehydes in the tissue of interest. Of particular interest are those genes encoding one or more enzymes capable of metabolizing a precursor compound required for the biosynthesis of cinnamic and/or coniferyl aldehyde and/or HCA from substrates normally found in a plant cell, more particularly the transgenic expression of at least one compound of the formula (1), (2), (3), (4), or (5).

Of particular interest are gene control regions that selectively regulate structural gene expression in a plant, plant part, plant cell, specific plant tissue and/or are associated with a particular stage of plant growth. Preferred are those control regions, and in particular, transcriptional control regions or promoters, that are known in the art, that can be used to modulate the expression of a gene encoding an enzyme required to control the level of a compound of formula (1), (2), (3), (4) and/or (5) in a plant, plant part, plant cell, or specific plant tissue and/or are associated with a particular stage of plant growth. For example, promoters showing differential expression patterns in fruit are described in U.S. Pat. No. 4,943,674 and U.S. Pat. No. 5,175,095; in seed in U.S. Pat. No. 5,315,001; and in rapidly developing tissues and tender shoots in U.S. Pat. No. 5,177,011. Also see PCT/U.S.90/04066 which describes ovary tissue promoters which direct transcription in specific ovary tissues, including ovary pericarp. Expression in ovary pericarp tissue can result in expression in the edible portions of many fruits, including tree berries, drupes, druplets, hesperidium and pepos. In legumes, the equivalent tissue to the fruit is the seed pot. Expression of the structural gene in analogous structures of non-edible fruit also can be obtained. For example, in cotton the analogous ovary structure is the burr of the cotton ball; use of an ovary pericarp promoter thus provides for production of the compounds of interest in cotton fibers. PCT/U.S.90/04066 also discloses a promoter which results in increased expression and response to leaf wilting. Thus, depending upon the tissue and/or plant part typically infested by an agricultural pest, the compositions can be expressed in the most appropriate tissue(s) and/or plant part(s).

DNA constructs for expressing a gene of interest can be prepared which provide for integration of the expression cassette into the genome of a plant host. A recombinant DNA molecule is produced by operatively linking a vector to a useful DNA segment to form a plasmid that is then used for plant transformation. A vector which directs expression of RNA from a cloned portion of a gene is referred to herein as an "expression vector." Such expression vectors contain expression control elements including a promoter. Typical vectors useful for expression of genes in higher plants are well known in the art and include vectors derived from the Ti plasmid of *Agrobacterium tumefaciens* described by Rogers et al., *Methods in Enzymology* (1987) 153:253–277. Integration can be accomplished using transformation systems known in the art such as Agrobacterium, electroporation or high-velocity microparticle-mediated transformation. Depending upon the application, saponin or one of the other compounds of interest can be preferentially expressed in a tissue of interest and/or a particular organelle. Tissue specificity is accomplished by the use of transcriptional regulatory regions having the desired expression profile. Translocation of the enzyme to a particular organelle is accomplished by the use of an appropriate translocation peptide. Methods for tissue and organelle specific expression of DNA constructs have been described and are known in the art.

A number of different transformation methods are available for the routine transformation of a wide range of plant species. One method that is particularly efficient for the transfer of DNA into dicotyledonous plants involves the use of Agrobacterium. In this method the gene of interest is inserted between the borders of the T-DNA region that have been spliced into a small recombinant plasmid with a selectable marker gene (for example encoding neomycin phosphotransferase II or phosphinothricin acetyltransferase). The recombinant plasmid is then introduced into an Agrobacterium host by transformation or triparental mating. The Agrobacterium strain carrying the gene(s) of interest is then used to transform plant tissue by co-culturing the bacteria with an appropriate plant tissue (e.g., leaf disc). Transformed cells are selected in tissue culture using the appropriate selection agent and plants are then regenerated (see Horsch, R. B. et al., *Science* (1985) 227:1229–1231). Other methods that have been used in the transformation of plant cells, and in particular the more recalcitrant crop plants, include biolistics and electroporation (for detailed protocols, see Sanford, et al., (1993) *Methods in Enzymology* 217:483–509; and Potter, (1993) *Methods in Enzymology* 217:461–478.

Once transgenic plants have been produced, conventional enzyme assays for CA4H and CAD are used to determine the level of suppression of enzyme activity achieved in different transformants. It is likely that only a small fraction of the transformants produced will have a sufficiently low residual enzyme activity to cause the accumulation of aromatic aldehydes without also producing some undesirable side-effects on plant development. For this reason, a preferred method of producing the desired transformants with both CA4H and CAD suppressed is to introduce the two genes separately into different transformants and then combine them by standard sexual crosses. This permits a larger number of combinations of level of gene suppression to be evaluated at the same time.

To verify regulation and expression of the gene of interest, various techniques exist for determining whether the desired DNA sequences present in the plant cell are integrated into the genome and are being transcribed. Techniques such as the Northern blot can be employed for detecting messenger RNA which codes for the desired enzyme. Expression can further be detected by assaying for enzyme activity or immunoassay for the protein product. Most preferably the level of the compound of interest present in a plant host is measured using methods known in the art. A desired phenotype, for example, is increased HCA content in a plant tissue of interest as measured by expression of the gene of interest and/or the level of HCA present in the plant host as compared to a control plant.

An alternative to overproducing aromatic aldehydes in transgenic plants is to use the plant genes to confer on a microbial host the capability of synthesizing specific aromatic aldehydes. The resulting microbes can be used either to produce the aromatic aldehydes in a fermentation system or as a natural delivery system of the aromatic aldehydes in viable or non-viable microbial preparations. Yeasts, especially *Saachoromyces cerevisiae*, are preferred organisms for this purpose because they have already been engineered for high-level expression of PAL (Faulkener et al. (1994) Gene 143:13020) and a plant cinnamate 4-hydroxylase has been shown to function in yeast (Urban et al. (1994) *Eur. J Biochem.* 222:843–850).

The expression of PAL introduces the capability to produce cinnammic acid from phenylalanine. Two additional enzymic steps are required to produce cinnamaldehyde from phenylalanine. In plants, these steps are catalyzed by the enzymes cinnamate:CoA ligase (CL) and cinnamoyl:CoA reductase (CCoAR), but as 4-coumarate:CoA ligase (4CL) can also use cinnamic acid as a substrate (Knobloch, and Hahlbrock (1977) *Arch. Biochem. Biophys.* 184:237–248). 4CL can be used instead of CL. More than 20 cloned PAL genes and more than 6 4CL genes have been described in sufficient detail (GenBank) to facilitate their use in practicing the current invention. A gene for a CCoAR is obtained by applying standard gene cloning techniques to isolate a cDNA clone using as a probe sequence derived from the amino acid sequence of the N-terminus, or peptide fragments, of the purified protein. CCoAR has been purified and partially characterized from soybean cultures (Wengenmayer et al. (1976) *Eur. J Biochem*, 65:529–536; Luderitz and Grisebach (1981) *Eur. J Biochem*, 119:115–124), spruce cambial sap (Luderitz and Grisebach, supra), poplar xylem (Sarni et al. (1984) *Eur. J Biochem*, 139:259–265) and differentiating xylem of *Eucalyptus gunnii* (Goffner et al. (1994) *Plant Physiol.* 106:625–632). The preferred method of purification is that of Goffner et al. (supra) because it results in a single protein band on SDS-polyacrylamide gels that can be used for protein sequencing.

The cloned genes are introduced into standard expression vectors and used to transform a microbial host, preferably yeast, by standard transformation techniques such as electroporation (Becker and Guarante (1991) *Methods in Enzymol.* 194:182–187). Standard enzyme assays are used to confirm the functional expression of the engineered genes and assays for aromatic aldehydes are used to select strains with maximal production. Because aromatic aldehydes have antimicrobial properties it is preferred to use expression vectors that drive expression of the introduced genes only late in the growth cycle or in response to a chemical inducer. It may also be desirable to grow the engineered microbial host in an immobilized whole cell reactor (e.g., Evans et al. (1987) *Biotechnology and Bioengineering* 30:1067–1072) to prevent the aldehydes from accumulating in the culture medium.

The target insects and other pests include those which are vectors for disease organisms such as fungi which colonize a surface of a part of a plant which is an elicitor for the fungus and various bacteria. By elicitor is intended that the plant secretes nutrients required by the microorganism. Whether a given insect or other pest is repelled by the formulation and the amount required to repel the organism can be determined using methods known to those of skill in the art. The insect carriers for various fungal diseases which can be repelled by the subject formulations include beetles, bees, wasps, flies, aphids, leafhoppers and bugs. Examples of fungal infections which can be prevented by repelling the insect carrier and the plant parts which they colonize are as follows. Black spot on fruit; *Fusarium sp.* on flowers roots and leaves; and *Fusarium spp.*, Aspergillus on roots and leaves and *Eutypa sp.* on plants (e.g. grapes). Fusarium causes vascular wilts of annual vegetables and flowers, herbaceous perennial ornamentals, plantation crops and the mimosa tree. Different plants are attacked by special forms or races of the fungus. Verticulum (*V. albo-atrium* and *V. dahlise*) cause vascular wilts and colonize roots, flowers and leaves. In addition the following also constitute target organisms: *Phragmidium spp; Diplocaopan rosae; Sphaerotheca tannosa; Oibiapsis sicula; Phytophthora taraesitica; Phytophthora infestans, Puccinia spp; Alternaria spp; Susaiun spp; Botrytis cinera; Sclerotinia homoeocarca; Tricophyton mentagrophpytes; Ceratocystis ulmi* (Dutch Elm disease) and *C. fagacearum* (oak wilt). Ceratocystis causes vascular wilts, mainly of trees. Also included are blue-green algae (species of Cyanobacteria) which develops as a black scum on the surface of overly wet soils, the Bryophytes (.i.e. moss, liverworts, etc.) and the *Botista algae*. Some bacterial diseases and viral diseases of plants such as bacterial soft rot, Pierces' disease, Stewart's disease, cucurbit wilt, fire blight, olive knob, bacterial rot, curly top, bean mosaic, citrus tristeza, cotton leaf curl, cucumber mosaic, maize mosaic, maize chlorotic dwarf, onion yellow dwarf, pea enation mosaic, potato spindle tuber, potato yellow dwarf and rice dwarf are insect-borne diseases.

Target organisms also include insects which damage the plants which they colonize, particularly those of the orders Orthoptera; Thysanoptera which includes water weevil and thrips; and Homoptera which include aphids such as root aphid and leaf aphid, leafhoppers, white flies, mealy bugs, thrips, cicadas, caterpillar, such as velvet bean caterpillar, codling moth, leaf roller, and scale insects. Other target organisms include arachnids (particularly spider mites), flies (Muscidae), cockroaches, gastropods, moths, and bed bugs (Cimex lectularis) and their close relatives, the poultry bug (Haematosiphon indorus Duges), the European pigeon bug (Cimex columbarius Jerjus), the swallow bug (Oeciains vicarius Hrovath), silver leaf whitefly, Japanese beetle, mole crickets and mealybug. The subject formulations also are useful for treating: grape to repel pests such as thrips, nematodes, and leaf roller; roses to repel thrips and melon aphids; cattle to repel soft ticks; humans to repel mosquitos; apple to repel codling moth; animals to repel fleas and chigger mites; cockroach habitats to prevent or eliminate cockroach infestation by repelling cockroaches already present; and corn to repel root aphids.

Additional target organisms include lice, particularly the suborders of Anoplura and Mallophaga. Species of *Pediculus humanus, Pediculus capitis, phthirus pubis* belong to the genus Pediculus, suborder Anoplura, and are parasites on humans, chimpanzee, spider monkeys, gibbons and the great apes. Other suborder Anoplura lice include the families Haematopinidae, Linonathidae, Solenopotes which are found on domestic animals. Target lice in suborder Mallophaga include *Menacanthus stramineus* (chickens and poultry species); livestock biting lice (mammals); *Damalinia bovis* (cattles); *Damalinia equi* (horses); *Damalinia ovis* (sheep); *Damalinia caprae, Damalinia crassipes, Damalinia limbata* (goats); *Heterodoxus spiniger, Trichodectes canis* (dogs) and *Felicola subrostrata* (cats).

In order to determine the susceptibility of particular insects and other pests to repellency by the claimed compositions, in vitro and in vivo tests which compare the behavior of the target pest towards, for example, approaching a "bait" food in the presence and absence of the test composition are used. The effectiveness of the formulation over time can be evaluated by extending the time period of observation until few of the test insects (less than about 50%) are repelled from the vicinity of the bait. For pathogen vector insects, a 90% or greater repellency is preferred, 90–100% more preferred andI 100% most preferred. For the common nuisance pest, reduction in the number of pests by about 80% or greater is preferred (e.g., in garden and food areas). The formulations also need to be evaluated for phytotoxicity for use on plants and for dermal sensitivity, particularly for use on skin and/or clothing of humans; contact dermatitis and olfactory sensitivity are monitored using tests for dermal sensitivity known to those of skill in the art. It is preferred that the formulations do not cause contact dermatitis in normal individuals. Likewise, phytoxicity testing can be done using methods known to those of skill in the art. Phytotoxicity can be rated as follows in order of increasing severity of toxicity: 0-plants without any symptoms; 1-very slight browning of hypocotyl (no other symptoms); 2-some wilting of plant, dying of lower leaves, some browning of vascular system; 3-wilting of entire plant, leaves dying, hypocotyl with external and internal symptoms; 4-necrosis of stem, plant dying. It is preferable that the formulation used have a phytotoxicity rating of 2 or less, more preferably 1 or less where the appearance of the plant or plant part is important, for example, ornamental trees, cut flowers, fruit, and the like.

The components of a formulation to be used for a particular application can be determined by evaluating first the concentration range over which a given component has no activity to where it provides maximum activity (a dose response curve) and then evaluating each component separately and in combination with other components of interest for a given formulation. The repellent effect on a given insect or other pest and/or phytotoxic and/or dermal effects of a particular formulation on the host plant or animal is then determined for each formula and component with or without a serial diluent of any additional component of interest. Optimal dose-ranges are calculated in vitro and in vivo using techniques known to those of ordinary skill in the art. Levels of penetration and evaporation of the subject compositions also can be determined by techniques known to those of skill in the art. For example, radio-labeling of a component of the composition (e.g. HCA) followed by measurement of radioactivity would enables one of skill in the art to determine levels of the composition following skin penetration and/or evaporation experiments. Publications relating to skin penetration experiments include Reinfenrath, WG and GS Hawkins. *The Weanling Yorkshire Pig as an Animal Modelfor Measuring Percutaneous Penetration. In: Swine in Biomedical Research* (M. E. Tumbleson, Ed.) Plenum, N.Y., 1986, and Hawkins, G. S. *Methodology for the Execution of In Vitro Skin Penetration Determinations. In: Methods for Skin Absorption*, B. W. Kemppainen and W. G. Reifenrath, Eds., CRC Press, Boca Raton, 1990, pp. 67–80; and W. G. Reifenrath, *Cosmetics & Toiletries*, 110, pp. 3–9 (1995).

Of interest are formulations containing HCA and stabilizing agents which can be applied directly to skin using any of the above-mentioned methods to repel a pest. The stabilizing agents in the formulations preferably decrease the level of HCA penetration into the skin. This is preferred because HCA finctions most effectively on the skin when present on its surface. It is evaporated HCA which repels insects and other pests. Since evaporation occurs only while HCA is on the surface of the skin, it is advantageous to have formulations that minimize penetration of the surface of the skin. Furthermore, minimizing HCA penetration minimizes any potential side effects caused by HCA. The theoretical evaporation of a chemical from a skin surface depends on its vapor pressure, but the actual evaporation rate also depends on ambient conditions (such as temperature, humidity and air speed) and on its interaction with the vehicle in the formulation and the skin surface (such as binding, a chemical reaction or penetration). (See Reifenrath, *Cosmetics & Toiletries*, 110, p 3–9, 1995).

Preferred formulations containing HCA and stabilizing agents which find use in the subject invention are those which effectively decrease the rate of evaporation of HCA to approximate the minimum effective evaporation rate (MEER). HCA is a low to moderately volatile compound, having a vapor pressure of $70 \times 10^{-5}$ mm Hg at 25° C., which is lower than the vapor pressure of DEET ($167 \times 10^{-5}$ mm Hg). Once HCA is formulated by the subject invention, the evaporation rate is further decreased. The stabilizing agent preferably not only reduces the evaporation of HCA but does so with zero order kinetics; i.e. evaporation of the HCA occurs at a constant, linear rate over time. Prolonged activity is obtained when a formulation exhibits zero order kinetic reactions. This zero order kinetics of evaporation is preferred over the evaporation profile of a non-stabilized HCA formulation which initially evaporates rapidly, and then the rate of evaporation decreases over time (first order). Preferably the formulations are stable at temperatures of up to 40° C. for at least one month. Examples of stabilizing agents which can be used in the HCA formulation to decrease the evaporation rate of HCA are polymers. Polymers useful for this invention generally have the characteristics of being raw material for topical composition, agent for gels and emulsifiers. If a polymer can make repellent chemical more efficacious, then the polymer is unique. Such polymer includes ethyl ester of polyvinyl methyl ether/maleic anhydride (PVM/MA) copolymer (Gantrez ES 225), dimethicone copolyol (ABEL 88183), polyacrylamide and C13–14 isoparaffin and Laureth-7 (Sepigel 305), propylene glycol and diazolidinyl urea and methylparaben and propylparaben (Germaben II), acrylates/C10–30 alkyl acrylates crosspolymer (Pemulen TR-1, NF), polyvinyl pyrrolidone (PVP)/eicosene copolymer (Ganex V-220), polyglyceryl-4-isostearate and cetyl dimethicone copolyol and hexyl laurate (ABIL WE-09), cetyl dimethicone (ABIL-Wax 9801), and dimethicone. Other substances such as propylene glycol, disodium EDTA, sodium chloride, glycerin, silica, water, mineral oil, triethanolamine and DEA—Cetyl phosphate (Amphisol) can be included in the HCA formulation.

To optimize the formulation, the Minimum Effective Dose of HCA against a pest is determined using the olfactometer/excised pig skin model as described in Reifenrath, *Cosmetics & Toiletries*, 110, p. 3–9, 1995). Target pests include mosquitoes and mites. The Minimum Effective Dose of HCA is determined as the concentration of HCA required to repel 100% of a pest over the assay time course. After determination of the Minimum Effective Dose of HCA, the Minimum Effective Evaporation Rate (MEER) of HCA at the Minimum Effective Dose is measured. The MEER is physically measured according to the Reifenrath method using a pig skin penetration/evaporation apparatus. The preferred formulation alters the HCA evaporation rate to approximate and exceed MEER. By experimental evaluation of each polymer, an optimal concentration is determined. The preferred formulations also are screened for threshold repellency and duration of repellency against a target pest using the olfactometer/excised pig skin model (Reifenrath). The candidate product formulations are then screened for compatibility with surfaces to which they may be applied (e.g., living surfaces such as animal skin and plant surfaces, plastic, wood, paint, etc.), followed by subsequent verification that efficacy and safety has not been changed with any formulation modifications.

The stability of the formulations over time can be evaluated using gas chromatography (GC) techniques using methods known to those skilled in the art. Stability of the formulation also can be evaluated using accelerated tests in which a formulation of interest is exposed to elevated temperatures over a set time. Samples of the formulations are taken at regular intervals and analyzed chemically by methods known to those skilled in the art to determine the rate and nature of degradation. For example, HCA can be analyzed by Gas Liquid Chromatography (GLC), using a 30 meter non-polar polydimethylsiloxane capillary column (e.g. HP-1, HewlettPackard, or SPB-1, Supelco) and a flame-ionization detector (Personal Communication). Using helium as a carrier gas (8 ml/min.) and a column temperature of approximately 240° C., the (E)-cis isomer (major component) has a retention time of approximately 6.0 minutes and the (Z)-trans isomer (minor component) has a retention time of approximately 6.3 minutes. Methanol or alcohol extractions of the formulations also can be prepared for HPLC analysis. The stabilizing agents also preferably increase the stability of the HCA-containing formulations, both physically and chemically. All formulations generally are stable when stored at room temperature (19°–21° C.) for at least one month.

In use, the compositions can be applied in a variety of ways depending on the intended use, for example by spraying, pouring, dipping, injecting, and fumigating, and can be in the form of concentrated liquids, solutions, suspensions, powders and the like. Particular interest includes delivery with wax suspension such as mineral , animal and plant wax; examples of plant wax are Carnauba, Candelilla and the like. The composition contains such concentration of the active compound as is most suited for a particular purpose at hand (see for example, U.S. Pat. No. 4,978,686 and Japanese Patent No. 1261303). For treating plants, the compositions can be applied, for example, in the form of a dilute solution for foliar application; in a suitable solvent as part of an irrigation schedule or as a separate application. For applications where the formulation is to be used to prepare the ground or other growth substrate for planting of host plants susceptible to particular pathogens, particularly where the growth substrate is already infested, the formulations of the subject invention can be added directly to the rhizosphere or the substrate or they can be bound reversibly to a solid support (see, for example, U.S. Pat. Nos. 5,202,247 and 5,340,731) or encapsulated in a time release material to repel undesirable insects and other pests. Where a solid carrier is used, materials which can lead to oxidation of the active aldehydes should be avoided. Examples of delivery systems which can be used include starch-dextran, and the like. See Yuan et al., *Fundamental and Applied Toxicology* (1993) 20: 83–87 for other examples of appropriate materials. The preferred method of repelling phylloxera and other root dwelling pests, however, is to provide for a systemic response to, for example, a foliar application of the formulation which is then translocated or induces resistance to the root. The timing of such applications is determined empirically for particular plants as the flow of water from the leaves to the roots is required for translocation or to signal an induce response. Generally, such flow is greatest at cooler temperatures e.g. during the evening hours, at night, or in the early morning hours, and pre or post fruit or vegetable development.

In addition to treating a host plant, seeds also can be treated using the subject formulations to repel insects and other pests which attack the seeds and/or which act as vectors for disease organisms. The seeds can be dusted with a powder preparation (see U.S. Pat. No. 4,978,686 for examples of inorganic materials to which the formulations can be absorbed) or admixed in a plant substrate such as vermiculite. Seedlings grown under sterile conditions from treated seeds are free of susceptible fungi and insects. Additionally, seedlings also can be treated with the subject formulations. In some instances it may be necessary to adjust the treatment formulation so as to reduce any phytotoxicity associated with the treatment as tender young shoots are more likely to exhibit phytotoxicity symptoms. The treatment formulations are also useful for controlling the time of pollination of flowering plants. For example, to prevent or delay pollination the formulations are applied in an amount sufficient to repel bees and other pollinating insects. By adjusting the residuality of the formulation, the length of time during which pollination is inhibited is controlled. On the other hand, for plants for which cross-pollination is required for fertilization, application of the formulation during this period should be avoided if the pollinating insect is repelled by the formulation.

When treating an area of pest infestation or an area susceptible to infestation other than an agricultural area, the formulation can be applied to the surface, such as a carpet, pet bedding, pet fur, clothing, skin, and the like. The compositions can be formulated as an aqueous solution. The formulations also can be used as powders, soaps, detergents or shampoos for treatment of infestations of animals or humans, including infestations with lice, fleas and ticks. The formulation can be prepared to include active compounds and anionic detergents such as those described in U.S. Pat. No. 4,978,686. In some instances it may be necessary to adjust the treatment formulation so as to reduce any dermatological effects associated with the treatment. Generally, the formulations are safe for ingestion and additionally, typically have positive organoleptic and olefactory characteristics. When repelling lice such as head lice from human, and body lice from mammals, the formulation in the form of shampoo, soap bar or the like, can be topically applied to the host. The hair, fur or body of the host can be washed with shampoo or soap comprising the repellent formulation. A preferred composition for repelling lice from mammals includes α-hexyl cinnamic aldehyde and saponin. The preferred concentration of HCA is about 0.01 to 20% and saponin is about 0.1 to 10% by weight of the total composition. More preferably, the HCA and saponin concentrations are about 1 to 20% and 1 to 10%, respectively.

The HCA formulations which include stabilizing agents can be used for treating animal dermal or keratinous surfaces. Moreover, such formulations can be applied to other materials made from natural or synthetic materials (e.g., cotton, cellulose, rayon, spandex, leather, etc.) that are used to protect animals (e.g., clothing, blankets, tenting, bedding and screening). When used in a solid form or microencapsulated, the dosage used is typically on the order of 1% to 35% on a w/w basis, the maximum loading to be determined as a function of shell material selected. Analytical chemical techniques are used to determine and optimize the rate of release for a particular application and/or target pest. For qualitative purposes, GC techniques can be used to determine the amount of aldehyde released. The samples of encapsulated (pelletized) product are mixed with the soil types selected and sampled at different time periods to measure release. Alternatively, the volatile gases released from the formulation also can be analyzed.

The components of a formulation to be used for a particular application can be determined by evaluating first the concentration range over which a given component has no activity to where it provides maximum activity (a dose response curve) and then evaluating this component separately and in combination with other components of interest for a given formulation. The repellent and/or phytotoxic and/or dermal effects of a particular formulation on a given insect or other pest and the host is then measured for each formula and component with or without a serial diluent of any additional component of interest. Optimal dose-ranges are calculated in vitro and in vivo using techniques known to those of ordinary skill in the art. Formulations are identified which provide: repellency of 90%, and/or a phytotoxicity rating of 2 or less for plants, with 1 or less being optimum, and substantially free of contact dermatitis for animals and fowl.

The following examples are offered by way of illustration and not by way of limitation.

| | |
|---|---|
| Example 1 | Flies (*Musca domestica*) |
| Example 2 | Cockroaches (*Blatella germanic*) |
| Example 3 | Aphid (*Aphid fabae*) |
| Example 4 | Silverleaf White Fly (*Tetranychus urticae*) |
| Example 5 | Leafhoppers (Cicadellidae) |
| Example 6A | Thrips (Thysanoptera) - cinnamic aldehyde |
| Example 6B | Thrips (Thysanoptera) - coniferyl aldehyde |
| Example 7 | Twospotted Spider Mite (*Tetranychus urticae*) |
| Example 8 | Mosquito (*Aedes aegypti*) |
| Example 9 | Lepidopteran ovipositional Repellency |
| Example 10 | Treatments of Grapevine Leaves for Control of Root Forms of Grape Phylloxera |
| Example 11 | Overproduction of Aromatic Aldehydes in Transgenic Plants |
| Example 12 | Production of Aromatic Aldehydes in Microbial Systems |
| Example 13 | Determine the Median Effective Dose of HCA against *Aedes Aegypti* |
| Example 14 | HCA Activity as Mosquito Repellent |
| Example 15 | Insect Repellent Solution, 5% (PG2A) |
| Example 16 | Insect Repellent Gel, 5% (JG6G) |
| Example 17 | Insect Repellent o/w, 5% (AG15B) |
| Example 18 | Insect Repellent w/o, 5% (AG14C) |
| Example 19 | Insect Repellent Ointment, 5% (OG3G) |
| Example 20 | Synthesis of $^{14}$C-labeled α-Hexylcinnamaldehyde |
| Example 21 | Physical Stability of α-Hexylcinnamaldehyde Formulations |
| Example 22 | Chemical Stability of α-Hexylcinnamaldehyde in Formulations |
| Example 23 | Skin Penetration and Evaporation of $^{14}$C-HCA in Formulation |
| Example 24 | Evaluation of HCA Formulations as Chigger Mite Repellents |

MATERIALS

The following products were used in the example protocols set forth below: (1) cinnamic aldehyde from Spectrum Chemical Co., New Jersey, USA; (2) coniferyl aldehyde from APIN Chemical Co., NK; (3) sodium bicarbonate and Tween 80 from Spectrum Chemical Co., New Jersey, USA; α-hexyl cinnamic aldehyde (Firmenich) New Jersey.

EXAMPLE 1

Flies (*Musca domestica*)

The purpose of this experiment is to evaluate the repellency activity of cinnamic aldehyde and α-hexyl cinnamic aldehyde against flies (Musca domestica). Twenty 2–3 day old female flies are released in a 62×62×34 cm cage with 325 mesh roof screening to permit air circulation (Carolina Biological Supplies). Bait made of sweet milk (Carnation) (90%) plus glucose (10%) and a dye (bromophenol blue 0.01%) with 1 ml of formulation is placed in a 3.5 cm petri dish and set inside a pine cage (Carolina Biological Supplies) with a 1 cm inch diameter hole drilled through the top to permit access to the cage containing the bait. A 3.5 cm petri dish with 5 ml $H_2O$ is placed in the cage for water. After 24 hours, flies are removed and crushed on filter paper to check for the presence of dye which would indicate feeding activity. Entry of more than 10% of the flies is taken as an indication of lack of formula repellent activity.

EXAMPLE 2

Cockroaches (*Blatella germanic*)

The aim of this experiment is to evaluate the repellancy activity of cinnamic aldehyde formula against cockroaches (*Blatella germanic*). Fifty nymphs and adults 1.5 cm to 3.5 cm in length are released in a 62×62×34 cm cage with 325 mesh roof screening to permit air circulation. The inner surface of the cage walls from 5 cm to 10 cm from the floor are treated with a mixture of mineral oil and petroleum jelly (2:3) to prevent escape of the cockroaches. The cockroaches are fed on dog chow (Purina), milk powder and water for 48 hours for acclimatization. Two Whatman filter papers "C" (4×4 cm) are folded twice, and stapled and wet with 1 ml of formula each. Filter papers are allowed to air dry. After air drying, a filter paper is placed inside of one of two 4 cm×4 cm×4 cm cubes, each with a single 0.75 cm door at floor (base) level for entry. The two shelter boxes are placed on the bottom floor of the cage 14 cm apart. After twenty hours, the shelters are removed and the number of shelter cockroaches are removed and counted. An entry of more than 10% of cockroaches into the shelter boxes is regarded as an indication of loss of formula repellency.

EXAMPLE 3

Aphid (*Aphid fabae*)

The purpose of this experiment is to determine the repellancy activity of a cinnamic aldehyde formulation against black bean aphids. Rose plants (miniature parade rose) are grown in 7.5 mm pots in potting soil in a greenhouse. At 16 weeks, 12 plants are selected at random. In separate trials, four plants are treated with: A (cinnamic aldehyde at 1000 ppm in emulsion with 500 ppm Tween 80); B (formula blank, Tween 80 only) and C (negative water control). Treatment is a foliar application of 5 ml of material sprayed as fine mist by a hand sprayer (Gilmour) until run off. The treated and untreated plants are placed in two rows, A, B and C, treated or untreated, respectively, in a 60×60×30 cm box cage with a 325 mesh screen roof permitting air circulation. Sufficient aphids were introduced from insectory to box cage. At 4, 8 and 24 hours, the number of aphids on treated and untreated plants, rows A, B and C, are counted and recorded.

EXAMPLE 4

Silverleaf White Fly (*Tetranychus urticae*)

The purpose of this experiment is to determine the repellency of cinnamic aldehyde against silver leaf white fly. In a greenhouse, cotton plants are grown in 7.5 mm pots in potting soil. When plants reach the three leaf stage, 12 plants are selected at random. In separate trials, four plants are treated with: A (cinnamic aldehyde at 1000 ppm in emulsion with 500 ppm Tween 80); B (formula blank, Tween 80 only) and C (negative water control). Treatment is a foliar application of 5 ml of material sprayed as fine mist by a hand sprayer (Gilmour) until run off. The treated and untreated plants are placed in two rows, A, B and C, treated or untreated, respectively, in a 60×60×30 cm box cage with a 325 mesh screen roof permitting air circulation. A sufficient population of silver leaf white fly are introduced from insectory to box cage. At 4, 8 and 24 hours, the number of silverleaf white flies are counted for presence on plants in rows A, B and C (treated and untreated). At 48 hours, the number of eggs on plants in each row are counted and recorded.

EXAMPLE 5

Leafliopers (*Cicadellidae*)

The purpose of this experiment is to determine the repellency of cinnamic aldehyde against leafhoppers. In a greenhouse, grape plants (Merlot) are grown in 7.5 mm pots in potting soil. When plants reach the three leaf stage, 12 plants are selected at random. In separate trials, four plants are treated with: A (cinnamic aldehyde at 1000 ppm in emulsion with 500 ppm Tween 80); B (formula blank, Tween 80 only) and C (negative water control). Treatment is a foliar application of 5 ml of material sprayed as fine mist by a hand sprayer (Gilmour) until run off. The treated and untreated plants are placed in two rows, A, B and C, treated or untreated, respectively, in a 60×60×30 cm box cage with a 325 mesh screen roof permitting air circulation. A sufficient population of leafhoppers are introduced from insectory to box cage. At 4, 8 and 24 hours, the number of leafhoppers are counted for presence on plants in rows A, B and C (treated and untreated). At 48 hours, the number of eggs on plants in each of the rows is counted and recorded.

EXAMPLE 6

Thrips (Thysanoptera)
(A) Cinnamic Aldehyde

The purpose of this experiment is to determine the repellency of cinnamic aldehyde against thrips. In a greenhouse, rose plants (miniature, parade rose) are grown in 7.5 mm pots in potting soil. At 16 weeks, 12 plants are selected at random. In separate trials, four plants are treated with: A (cinnamic aldehyde at 1000 ppm in emulsion with 500 ppm Tween 80); B (formula blank, Tween 80 only) and C (negative water control). Treatment is a foliar application of 5 ml of material sprayed as fine mist by a hand sprayer (Gilmour) until run off. The treated and untreated plants are placed in two rows, A, B and C, treated or untreated, respectively, in a 60×60×30 cm box cage with a 325 mesh screen roof permitting air circulation. A sufficient number of thrips are introduced from insectory into cage for trial. At 4, 8 and 24 hours, the number of thrips are counted for presence on plants in rows A and B (treated and untreated). At 48 hours, the number of eggs (in leaf slits) on plants in each row are counted and recorded.

(B) Coniferyl Aldehyde

Western Flower Thrips (Thysanoptera) were collected in the field on infested alfalfa (*Medicago sativa*). Alfalfa inflorescence were cut then dipped in either a coniferyl aldehyde formulation (2% coniferyl aldehyde, 1% Tween 80) or a water control, then were placed in an experimental arena (approximately 9 cm in diameter by 6 centimeter in height) on a Whatman filter paper disk covering the floor of the arena. Approximately fifty (50) to sixty (60) insects were aspirated into the experimental arena which was then covered with a transparent lid. Treated and controlled arenas were then observed for thirty (30) minutes for insect colonization and feeding on the alfalfa inflorescence. Repellency was determined by the relative number of individuals who successfully maintained feeding and colonization on the inflorescence over time. Repellency results are presented in Table 1. Coniferyl aldehyde formulation was repellent and lethal when contacted by insects.

TABLE 1

Coniferyl Aldehyde
Repellency to Western Flower Thrip

| Observation: | Treatment (2% Coniferyl Aldehyde) | Control (Water) |
| --- | --- | --- |
| Number of insects on inflorescence (colonization and feeding) | 2(dead) | 22(alive) |
| Length of insect residence time on inflorescence | 15 seconds(max) | 30 minutes |
| Description of insect behavior | Irritated by treatment, extreme agitation, frequent flying. No feeding. | Tranquil, normal flight, feeding |

EXAMPLE 7

Twospotted Sipider Mite (*Tetranychus urticae*)

The aim of this experiment is to evaluate the repellency of cinnamic aldehyde on twospotted spider mites. Rose plants (miniature parade rose) are grown in 7.5 mm pots in potting soil in a greenhouse. At 16 weeks, 12 plants are selected at random. In separate trials, four plants are treated with: A (cinnamic aldehyde at 1000 ppm in emulsion with 500 ppm Tween 80); B (formula blank, Tween 80 only) and C (negative water control). Treatment is a foliar application of 5 ml of material sprayed as fine mist by a hand sprayer (Gilmour) until run off. The treated and untreated plants are placed in two rows, A, B and C, treated or untreated, respectively, in a 60×60×30 cm box cage with a 325 mesh screen roof permitting air circulation. Sufficient twospotted spider mites are introduced from insectory to box cage. At 4, 8 and 24 hours, the number of spider mites are counted for presence on plants in rows A and B. At 48 hours, the number of eggs on plants in each row are counted and recorded.

EXAMPLE 8

Mosquito (*Aedes aegypti*)
Repellency Test Procedure In Vitro

The purpose of this experiment is to evaluate the repellency of cinnamic aldehyde against mosquitos. Twenty unblooded adult female mosquitoes approximately 4 days of age are introduced into test chambers. Four ml of a test formulation is pipetted onto a 16 cm #2 Whatman filter paper circle and air dried. The treated filter paper is placed on the vent intake chamber. $CO_2$ is bubbled through water at the vent intake end of a wind tunnel olfactometer chamber; the lowest rpm fan setting is used. The trap chamber is opened for 5 minutes, then closed and the number of mosquitoes counted and recorded. Water is used as an untreated control.

Repellency Test Procedure, Field Trial

The purpose of this experiment is to bioassay the activity of cinnamic aldehyde as a mosquito repellent. Two circles 18 cm in diameter and two 16 cm in diameter were cut from 1 mm mesh nylon mosquito cage bolt of screen material. The treatment circle (16 cm) was soaked in 1 ml formulation: cinnamic aldehyde (2%) in 2% Tween 80 and 6% $NaHCO_3$, then allowed to air dry for 2 hours. Ten unfed female *Aedes aegypti* mosquitoes (5–7 days old) from the Kearney Agriculture Center, Mosquito Control Research Laboratory, were introduced into each of two Kearney (Fischer) one pint mosquito cartons (control and treatment cartons). Each carton was covered with one of the untreated 18 cm circle mesh screens and sealed with a rim from the pint carton, the lid section having been removed. An adult male volunteer placed the treated 16 mm circle on one of his legs (which had been washed and rinsed with soap and water) and the untreated 16 mm circle on the other leg (washed and rinsed with soap and water). The one pint mosquito cartons were put in flush contact with the mesh screen side to the leg screen patches for 5 minutes. Mosquitoes did not come in direct contact with the leg screen patches. After 5 minutes, the number of blooded/well-gorged insects out of 10 in the cartons were counted. The results are shown in Table I, below. Out of a total of thirty insects evaluated, only two were not repelled by the cinnamic aldehyde formulation, as compared with 19 in the control (untreated) group.

TABLE 2

Mosquito Repellency
(# of blooded/well-gorged insects/10 insects)

| Treatment | Trial 1 | Trial 2 | Trial 3 | Sum |
| --- | --- | --- | --- | --- |
| Cinnamic aldehyde formulation[1] | 0/10 | 2/10 | 0/10 | 2/30 |
| Control (untreated) | 5/10 | 7/10 | 7/10 | 19/30 |

[1]Cinnamic aldehyde (2%) with 2% Tween 80, and 6% $NaHCO_3$ in $H_2O$.

A protocol similar to that described above is used to test α-hexyl cinnamic aldehyde. The HCA results are shown in Table 3. Out of a total of 20 insects evaluated, all were repeled by the HCA formulation, as compared with only 2 were repeled in the control group.

TABLE 3

α-hexylcinnamicaldehyde (HCA) against *Aedes aegypti*

| Treatment | Number Blooded Mosquitoes/Total Mosquitoes | |
| --- | --- | --- |
| | Trial | 5 Minutes |
| HCA Formulation[1] | 1 | 0/10 |
| | 2 | 0/10 |
| $H_2O$ Control | 1 | 9/10 |
| | 2 | 9/10 |

[1]HCA (5%) with 2% Tween 80 in $H_2O$.

EXAMPLE 9

Lepidopteran Ovipositional Repellency

The purpose of this experiment is to determine the repellency of cinnamic aldehyde against Beet Armyworm adult moths. An apparatus is built that forces an airstream over treated and non-treated potted plants in a flight cage. Five tomato plants at the three leaf stage are treated with 5 ml of various concentrations of chemical formula and components and then placed in the cage. Five tomato plants are sprayed with 5 ml of $H_2O$ as control plants and then placed in the cage. Forty egg laying ready Beet Armyworm (*Spodoptera exigna*) adults are released in the cage. The exhaust fan on the apparatus is turned on and a low velocity linear flow of air is allowed to flow through the cage as plumelets of air to evaporate the chemical formula. After 24 hours, oviposition is determined on treated plants, non-treated plants, and cage walls.

EXAMPLE 10

Treatments of Grapevine Leaves for Control of

Root Forms of Grape Phylloxera

The root form of grape phylloxera (*Daktulosphaira vitifoliae* Fitch) is arguably the most devastating grape insect world wide. In this experiment, cinnamic aldehyde formulated with 1% Tween 80 was tested for ability to control phylloxera. One year old potted *V. vinifera* cultivar merlot plants were used that had been obtained from Foundation Plant Material Service, University of California, Davis. The plants were potted in 10 cm diameter ports and were infested with phylloxera 5 weeks prior to treatment. At the time of spraying, plant pots were placed in a plastic bag so that chemical runoff from the leaf sprays would not drip into the soil. Spray was applied to runoff with a household 1 liter-capacity plastic spray bottle. Plants were allowed to air dry outside and then replaced in the greenhouse. At intervals thereafter, the roots were separated from the potting mix and total phylloxera population estimated.

Roots from plants at 5 weeks post-treatment were excised and 6 root sections, about 3 mm diameter by 4 cm length were cleaned of infestations and used in a bioassay. For this bioassay, root sections were inoculated with 20 eggs and the roots maintained as the colonies were maintained. After 25 days, the number of individuals of each age class were counted.

TABLE 4

Number of Phylloxera on 6 Root Sections Per Dosage

| Treatment | Eggs | 1st instar | 2nd instar | 3rd instar | 4th instar | Adults |
|---|---|---|---|---|---|---|
| Water | 52 | 7 | 7 | 7 | 13 | 16 |
| 300 ppm | 16 | 0 | 6 | 5 | 0 | 4 |
| 1000 ppm | 2 | 0 | 1 | 4 | 2 | 1 |
| 3000 ppm | 0 | 0 | 2 | 1 | 1 | 0 |
| 10,000 ppm | 0 | 0 | 2 | 0 | 0 | 0 |

When foliage of whole plants were treated with cinnamic aldehyde formulation, activity was translocated or induced as resistance to the roots. Vacant feeding sites were seen and the excised roots maintained resistance to phylloxera reinfestation for at least 5 weeks after treatment. The results suggest that the aromatic aldehyde and/or a metabolite is translocated to the roots where it directly kills phylloxera or repels phylloxera to vacate feeding sites. Alternatively, aromatic aldehyde induces the plant to change its root chemistry in a way that makes the roots unacceptable to phylloxera feeding. Either mechanism is an exciting new approach to control of grape phylloxera and other pest species. Conventional systemic insecticides are generally upwardly mobile in plants, not downwardly mobile; therefore this downward mobility is an important addition to the insecticidal arsenal. If the aromatic aldehydes are stimulants of induced host plant resistance, it adds a new approach to treatment of plant pests.

EXAMPLE 11

Overproduction of Aromatic Aldehydes in Transgenic Plants

Twenty mg of polyA RNA is prepared and cDNA synthesized. Part of this is cloned into a lambda-ZAP II vector (a commercially available cloning vector). At least 500,000 recombinants are screened using an oligonucleotide probe designed from conserved sequences of cloned CA4H and CAD genes obtained from GenBank, or designed from peptide sequence of purified protein from the intended host plant. Strongly hybridizing clones are selected and used to rescreen the cDNA library (see PCT W093/05159). The resulting clones are sequenced to enable the introduction of appropriate gene sequences into a plant expression cassette in either the antisense or the sense orientation. The antisense and sense constructs are introduced into *Agrobacterium tumefaciens* LBA4404 by direct transformation following published procedures. Tobacco (N. tabacum, variety Samsun) leaf discs are transformed using well estabished published procedures (Horsch et al. (1985) *Science* 227:1229–1231. Plants containing either CA4H or CAD constructs are identified by PCR and selected for further analysis.

Plant material from both transformed and untransformed control plants is used for determinations of CA4H and CAD enzyme activity using well established published assays (see PCT WO93/05159). Plants in which the activity of CA4H or CAD has been reduced to less than 20% of that seen in control plants are selected for further analysis. Selected plants with low CA4H activity are crossed with plants with low CAD activity and progeny inheriting both gene constructs are selected by PCR. Plants with suppressed CA4H and suppressed CAD activity are analyzed for aromatic aldehyde production using standard chemistry procedures. Those plants that produce aromatic aldehydes are then tested for efficacy of repelling insects or other pests using any appropriate example, e.g. Example 3 to test transgenic cotton plants for their capacity to repel aphids.

EXAMPLE 12

Production of Aromatic Aldehydes in Microbial Systems

A cDNA library is generated using RNA extracted from six week old tobacco stems. 20mg of polyA RNA is prepared and cDNA synthesized. Part of this is cloned into a lambda-ZAP II vector (a commercially available cloning vector). At least 500,000 recombinants [most organisms?] are screened using an oligonucleotide probe designed from peptide sequence sequences of CCoAr protein purified from six week old tobacco stem tissue using the protocol of Goffner et al. (1994) *Plant Physiol.* 106:625. Strongly hybridizing clones are selected and used to rescreen the cDNA library. The resulting clones are sequenced to enable the identification of full-length cDNA inserts and the introduction of appropriate CCoAR gene sequences into a yeast expression vector pMTL8110 (Faulkner et al. (1994) *Gene* 143:13–20. The coding sequences for Rhodosporidium toruloides phenylalanine ammonia lyase (PAL; GenBank locus RHDPAL) and a parsley 4-coumarate:CoAl ligase (4CL; GenBank locus PC4CL1AA) are similarly introduced into equivalent yeast expression vectors. The PAL,4CL and CCoAR constructs are used to transform *Saccharomyces cerevisiae* strains by electroporation using established published procedures (Becker, and Guarente, *Methods in Enzymology*

194:182–187, 1991; Simon (1993) *Methods in Enzymol* 217:478–483. Transformants are selected on minimal medium lacking leucine. Transformant strains carrying all three gene constructs are identified by PCR and selecter for further analysis.

Extracts from both transformed and untransformed control strains are used for determinations of PAL, 4CL and CCoAR enzyme activities using well established published assays. Strains in which the activity of PAL, 4CL and CCoAR is significantly greater than the background activity detected in control strains are selected for further analysis. Selected strains are analyzed for aromatic aldehyde production using standard published procedures and those producing significant amounts of cinnamaldehyde are selected for optimization of fermentation conditions. The resulting products are then tested for their efficacy in repelling insects and other tests using any of the described methods.

EXAMPLE 13

Determination of the Median Effective Dose of HCA to Repel *Aedes Aegpti*

Median Effective Dose ($ED_{50}$) is defined as the amount of chemical required to repel 50% of a target pest. The $ED_{50}$ of HCA against *Aedes Aegypsi* (yellow fever mosquito) was determined using a test system developed by Walter Reed Army Institute of Research. The test system used was a mosquito blood feeder, which includes a constant temperature water circulator to warm the blood in the feeder, and the test cage. The blood was maintained at 37°. The blood feeder has five circular blood reservoirs, each of which is filled with outdated blood obtained from the Walter Reed Army Medical Center and certified safe according to Blood Bank testing procedures. The blood was replenished with adenosine triphosphate (ATP), without which the mosquitoes will not feed freely. The blood-filled reservoirs were covered with a Bandruche membrane (a standard membrane barrier). The HCA formulation in acetone was applied on this membrane at random in dose response system to determine $ED_{50}$. DEET was used as a positive control in a similar manner. A negative control formulation (water only) also was tested. The mosquitoes were given access to the blood reservoirs on a "free feeding" basis by means of a sliding door in the bottom of the test cage. The $ED_{50}$ of HCA was found to be 0.0031 mg/cm² compared with an $ED_{50}$ of 0.0124 mg/cm² for DEET.

EXAMPLE 14

HCA Activity as Mosquito Repellent

The purpose of these experiments was to determine whether α-hexyl cinnamic aldehyde is an effective mosquito repellent.

Direct Skin Application

HCA was evaluated on the skin of 2 to 4 male human subjects. One ml of 100% HCA was rubbed over one forearm. A glove was worn to protect the untreated hand while the treated forearm was exposed in a cage containing a high number (2,000–4,000) of unfed mosquitoes for 3 minutes at intervals of approximately 30 minutes until two bites were received (two bites in one test period or one bite in each of two consecutive test periods). The time interval between application and when two bites were received was defined as the "protection time." The repellent classes based on protection time (minutes) are listed below:

TABLE 5

| | Protection Time (Minutes) | |
|---|---|---|
| Class[1] | Yellow fever and salt march mosquitoes | Common malaria mosquitoes |
| 1 | 0–60 | 0–30 |
| 2 | 61–120 | 31–60 |
| 3 | 121–180 | 61–90 |
| 4 | 180 or > | 90 or > |
| 4A | 300 or > | 150 or > |

[1]USDA rating scale.

Against the yellow fever mosquito (*Aedes aegypti* (L)), the protection time of HCA was rated as 3 (121–180 minutes duration), against the malaria mosquito (*Anopheles quadrimaculatus* Say), the protection HCA was rated as 2 (31–60 minutes).

Application to Clothing

HCA also was evaluated on treated cloth against the yellow fever mosquito. In these tests, women's mercerized-cotton stockings were used. A measured section above the ankle was impregnated with HCA at a rate equivalent to 3.3 g/ft². The stocking was spread on a rack to dry and then hung indoors on a line. The first tests were done 24 hours after treatment. The treated stocking was drawn over the arm, with the treated portion midway on the forearm. The untreated hand was protected with a glove and the stocking-covered arm was exposed for one minute in a testcage. If 5 bites were received, the treatment was considered ineffective. If less than 5 bites were received; the exposures were continued daily until the 14th day and at weekly or biweekly intervals thereafter. The protection time of HCA received a grade of 4 in this test (effective for more than 10 days).

EXAMPLE 15

Insect Repellent Solutions 5% (PG2A)

Phase A ingredients (see Table below) were added to the main vessel and mixed completely. The Phase B ingredients then were added and mixed completely, followed by addition of the Phase C incredients which were mixed in completely. The resulting product was a clear yellow syrupy solution at both ambient temperature and at 4° C.

TABLE 6

| PG2A | |
|---|---|
| Ingredient | Concentration (% w/w) |
| Phase A | |
| SD Alcohol 40-A | QSAD 100.00 |
| AMP-95[1] | 0.50 |
| Phase B | |
| Gantrez ES 225[2] | 20.00 |
| Phase C | |
| α-hexylcinnamaldehyde | 5.00 |
| ABIL B 88183[3] | 1.50 |

[1]Aminomethyl propanol, Angus Chemical Company.
[2]Ethyl ester of (PVM/M) polyvinyl methyl ether/maleic anhydride, copolymer, International Specialty Products.
[3]Dimethicone copolyol, Goldschmidt Chemical Corporation.

EXAMPLE 16

Insect Repellent Gel, 5% (JG6G)

Phase A ingredients (see Table below) were added to the main vessel. No heat was applied. Phase B ingredients were added slowly to the main vessel, with maximum agitation. Strong agitation was continued until Sepigel was completely hydrated. The Phase C and Phase D ingredients were then added in tandem; each phase mixed in completely. The resulting product was a light yellow, opaque, canary, glossy, thick but soft gel both at ambient temperature and at 4° C.

TABLE 7

| JG6G | |
|---|---|
| Ingredient | Concentration (% w/w) |
| Phase A | |
| Purified water | QSAD 100.00 |
| Phase B | |
| Sepigel 305[1] | 10.00 |
| Phase C | |
| α-hexylcinnamaldehyde | 5.00 |
| Phase D | |
| Germaben II[2] | 1.00 |

[1]Polyacrylamide (and) C13–14 isoparaffin (and) Laureth-7, Seppic.
[2]Propylene Glycol (and) diazolidinyl Urea (and) methylparaben (and) propylparaben, Sutton Labs, Inc.

EXAMPLE 17

Insect Repellent o/w, 5%, (AG15 SB)

Phase A ingredients were added to the main vessel and heated to 80° C. A chelating agent, disodium EDTA, was included in the phase A ingredients to avoid precipitation of calcium ions from water during preparation of the formulation. Phase B ingredients were added slowly to the main vessel, with maximum agitation. Strong agitation was continued until the Pemulen was fully hydrated. The temperature was maintained at 80° C. Phase C ingredients were added to a separate vessel and heated, with agitation, to 85° C. until complete dissolution of all ingredients was obtained. The Phase C ingredients then were added to the main vessel at 80° C. with strong agitation. Strong agitation was continued until a homogenous emulsion formed. Phase D was used to adjust the pH to between 6.0 and 6.5. The batch was cooled with occasional, gentle mixing, to 30° C. Phase E was added and mixed in completely. The resulting product was a white, opaque, stiff butter cream both at ambient temperature and at 4° C.

TABLE 8

| AG15B | |
|---|---|
| Ingredient | Concentration (% w/w) |
| Phase A | |
| Purified water | QSAD 100.00 |
| Propylene glycol | 5.00 |
| Disodium EDTA | 0.05 |
| Phase B | |
| Pemulen TR-1, NF[1] | 0.40 |
| Phase C | |
| Stearic acid | 3.00 |
| Cetyl alcohol | 2.00 |
| Octyl stearate | 4.00 |
| Amphisol[2] | 3.00 |
| Ganex V-220[3] | 10.00 |

TABLE 8-continued

| AG15B | |
|---|---|
| Ingredient | Concentration (% w/w) |
| α-hexylcinnamaldehyde | 5.00 |
| Phase D | |
| Triethanolamine/purified water | 2.00 |
| Phase E | |
| Germaben II[4] | 1.00 |

[1]Acrylates/C10–30 alkyl acrylates crosspolymer, BF Goodrich Specialty Chemicals.
[2]DEA-cetyl phosphate, Givaudin Corporation.
[3]Polyvinyl pyrrolidone (PVP)/eicosene copolymer, International Specialty Products.
[4]Propylene glycol (and) diazolidinyl urea (and) methylparaben (and) propylparaben, Sutton Labs, Inc.

EXAMPLE 18

Insect Repellent w/o, 5% (AG14C)

Phase A was added to the main vessel. It was heated to approximately 70° C. and mixed to melt and disperse the waxes. Once the waxes were melted and dispersed, mixing was continued until the temperature had cooled to 50° C. Phase B ingredients were added to a separate vessel, warmed to 40° C., and then mixed until the ingredients were completely dissolved. Phase B then was added to the main vessel using minimal agitation. Once all of Phase B has been added, agitation was increased; mixing was continued until an emulsion formed. The batch was cooled with gentle mixing, to 25° C., then the cream was homogenized with a rotor-stator homogenizer. The resulting product was an off-white, opaque, unctuous, thick, stiff cream both at ambient temperature and at 4° C.

TABLE 9

| AG14C | |
|---|---|
| Ingredient | Concentration (% w/w) |
| Phase A | |
| ABIL WE 09[1] | 5.00 |
| ABIL-Wax 9801[2] | 2.50 |
| Dimethicone, 100 cST | 5.00 |
| Castorwax[3] | 0.50 |
| Octyl stearate | 2.50 |
| Light mineral oil, NF | 2.50 |
| α-hexylcinnamaldehyde | 5.00 |
| Phase B | |
| Purified water | QSAD 100.00 |
| Glycerin, 99% | 3.00 |
| Sodium chloride | 0.50 |
| Germaben II[4] | 0.50 |

[1]Polyglyceryl-4 isostearate (and) cetyl dimethicone copolyol (and) hexyl laurate, Goldschmidt Chemical Corporation.
[2]Cetyl dimethicone, Goldschmidt Chemical Corporation.
[3]Hydrogenated castor oil, Caschem, Inc.
[4]Propylene glycol (and) diazolidinyl Urea (and) methylparaben (and) propylparaben, Sutton Labs, Inc.

EXAMPLE 19

Insect Repellent Ointment, 5% (OG3G)

Phase A ingredients were added to the main vessel and heated, with mixing, at 50° C. Once dissolution of the Ganex was completed. Phase B was added to the main vessel and mixed in completely. Phase C was added to the main vessel and mixed in completely. The batch then was cooled to 35° C. with occasional mixing. Phase D was added to the main vessel and mixed in completely. The resulting product was an orange/beige, translucent, stiff ointment.

TABLE 10

| Ingredient | Concentration (% w/w) |
|---|---|
| OG3G | |
| Phase A | |
| Light mineral oil, NF | QSAD 100.00 |
| Dimethicone 100 cST | 5.00 |
| Ganex V-220[1] | 10.00 |
| Phase B | |
| Bentone Gel MIO[2] | 30.00 |
| Phase C | |
| Syloid 244FP[3] | 15.00 |
| Phase D | |
| α-hexylcinnamaldehyde | 5.00 |

[1]PVP eicosene copolymer, International Specialty Products.
[2]Mineral oil (and) quaternium-18 Hectorite (and) propylene carbonate, Rheox, Inc.
[3]Hydrated silica, Davison Chemical.

EXAMPLE 20

Synthesis of (α-Hexylcinnamaldehyde-UL-ring-$^{14}$C

Ten mCi of the above radiolabaled compound was prepared from $^{14}$C-benzaldehyde and heptaladehyde by base catalyzed aldol condensation (see EP 329.579). (Wizard Laboratories, West Sacramento, Calif.). The specific activity was determined to be 2 mCi/mmole and the radiochemical purity was 99.7%. Chemical purity was 98.59% (GLC, both isomers) after dilution with unlabeled compound (Cat. No. 907.600, Firmenich, Inc., Princeton, N.J.).

EXAMPLE 21

Physical Stability of α-Hexylcinnamaldehyde Formulations

Five formulations (PG2A, JG6G, AG 15B, AG14C and OG3G) containing 5% HCA and ≧10% polymers were prepared (see Examples 15 to 19 above). Formulations JG6G (aqueous vehicle), AG15B (oil/water emulsion), AG14C (water/oil emulsion) and OG3G (anhydrous) underwent accelerated stability tests (40° C.×1 month). Formulation PG2A (alcohol solution) was not tested at elevated temperature due to its high alcohol content. No significant change of physical appearance of all formulation was observed after one month. AG 15B was slightly lumpy at the end of the elevated temperature period, but was similar to the control sample after cool-down. Observations of physical stability were as follows (Table 11).

EXAMPLE 22

Chemical Stability of α-Hexylcinnamaldehyde (HCA) in Formulations

Five formulations (PG2A, JG6G, AG15B, AG14C and OG3G) containing 5% HCA and stabilizing genes polymers were stored at room temperature (19° C.–21° C.) and samples were extracted 30 days later and analyzed by gas chromatography for HCA content.
Extraction Procedure A mass of 0.95–1.11 gram of each of the five formulations was placed in a liquid scintillation counting (LSC) vial. A mass of 1.08–1.15 gram of ethyl ether was added to each vial. Since formulation AG15B formed a gel with ethyl ether, an additional 1.16 gram of ethyl ether was used with this formulation. A magnetic stirring bar was placed in each vial and the contents of the vials stirred moderately overnight; vial caps were wrapped in parafilm as an additional seal to prevent loss of ether. After overnight stirring, 1.05–1.11 gram of ether was added to formulations PG2A, JG6G, AG14C and OG3G, so that the amount of ether added to all the formulations was nearly equivalent. The contents of the vials were stirred for an additional hour and then were left at room temperature for 4 days prior to GC analysis. On the day of analysis, the contents of the vials were rinsed into 5 ml volumetric flasks with ethyl ether. A theoretical concentration of 10 mg/ml would be obtained for the 5% (w/w) HCA formulations. However, formulations JG6G and AG 15B formed gels with ether, making it impossible to quantitatively transfer the vial contents to the volumetrics. For these formulations, volume was estimated as the sum of the volume of the formulation (using a density of 1 for the formulations and the known weight of the formulation added to the vials) and the volume of ethyl ether (using a density of 0.7134 g/ml for ethyl ether and the known weight of ether added to the vials). Theoretical concentration for the extracts was calculated by dividing the theoretical amount of HCA present in 1 gram of 5% formulation (50 mg) by the calculated volume of the ether gel.
Preparation of Standards HCA/Acetone solutions were prepared in the following concentrations: 1, 5, 10 and 20 mg/mL.

TABLE 11

| Formula Code | Initial Appearance (T = 0) | T = 1 Month |
|---|---|---|
| PG2A, Ambient | Clear, light yellow, syrupy solution | same as T = 0 |
| PG2A, 4° C. | Clear, light yellow, syrupy solution | same as T = 0 |
| JG6G, Ambient | Light yellow, opaque, bouncy, glossy, thick but soft gel. | same as T = 0 |
| JG6G, 40° C. | Light yellow, opaque, bouncy, glossy, thick but soft gel. | slightly yellower, otherwise same as T = 0 |
| AG15B, Ambient | White, opaque, stiff, buffer cream | same as T = 0 |
| AG15B, 40° C. | White, opaque, stiff, butter cream | some soft lumps, otherwise same as T = 0 |
| AG14C, Ambient | Off-white, opaque, unctuous, thick, stiff cream | same as T = 0 |
| AG14C, 40° C. | Off-white, opaque, unctuous, thick, stiff cream | slightly yellower, otherwise same as T = 0 |
| OG3G, Ambient | Orange/beige, translucent, stiff ointment | small amount of liquid oil on surface, otherwise same as T = 0 |
| OG3G, 40° C. | Orange/beige, translucent, stiff ointment | same as T = 0 |

Instrument Settings:

Gas chromatography used was Varian 3400 GC. Injector, column and detector temperatures for the GC were set at 200° C., 205° C., and 229° C. respectively. Carrier gas flow through the column was adjusted to 6.5 ml/min and make-up gas flow was set at 22.5 ml/min. The electrometer of the GC was set to an attenuation of 32 and the range was set at $10^{-11}$ amp/mv.

Injection Procedure:

Duplicate injections of 1.0 µl of HCA/Acetone standards were made. Single injections of 1.0 µl of ether extracts from formulations PG2A and AG14C were made. In the case of formulations JG6G and AG15B, single injections of 1.0 µl aliquots of the ether supernatant of the gels was injected. Duplicate injections of the ether extract from formulation OG3G were made. Typical retention times for the cis isomer were 4.63–4.81 minutes and 4.86–5.00 minutes for the minor trans isomer.

Calculations

The integrated area of HCA's major isomer (the cis isomer) was used in the calculations. For the standards, a calibration chart was constructed plotting integration area (y axis) against concentration in mg/ml (x axis). A linear regression analysis of the plot yielded the following equation y=1046x+65, with a correlation coefficient of 0.986. By substituting the observed integration area for "y", this equation was used to calculate the measured concentration (x) of HCA present in the ether extracts of the formulations. To calculate measured concentration, a volume of 5 ml was used for the ether extracts of formulations PG2A, AG14C, and OG3G. For formulations JG6G and AG15B, the volume calculated for the gels (see "Extraction Procedure") was used to calculate measured concentration.

The ratio of cis to trans area for formulations JG6G, AG15B, AG14C, and OG3G were 0.913, 0.918, 0.947, and 0.948 respectively. The trans peak in the chromatogram for formulation PG2A did not integrate. These ratios are in agreement with the product specifications from Firmenich (cis isomer, 93.8% maximum; trans isomer, 6% maximum).

Final Evaluation of HCA Content of Formulations:

Due to the difficulties encountered with gel formation during ether extractions of the formulations, a smaller amount of formulation was used (100 mg vs 1 gram) in the 5 ml ether extracts. Although radiolabeled HCA was not available at the time of this work, the use of the column outlet splitter to a trap will allow simultaneous radiometric and mass measurements in future studies.

The initial analysis of the HCA concentration in the five formulations was performed immediately after their preparation. Analytical results of all the formulation were within 92–104% of the expected concentration of 5% (Table 12).

TABLE 12

Initial Measurement of α-Hexylcinnamic Aldehyde (HCA) Concentration (% w/w) in Five Formulations

| Formulation Code No. | Measured Concentration (% w/w) |
|---|---|
| PG2A | 4.77 |
| JG6G | 4.52 |
| AG15B | 5.22 |
| AG14C | 4.61 |
| OG3G | 4.76, 5.05 |

After a 1 month storage of the 5 formulations at room temperature (19°–21° C.), mean HCA content of the five formulations ranged from 4.85 to 5.60% of the total weight of the formulations (Table 13). Samples of the four formulations which underwent the accelerated stability tests (40° C. for 1 month) also were extracted after one month and analyzed for HCA content. Mean HCA concentration of the four formulations after accelerated stabilizing testing ranged from 5.04 to 5.37% w/w. (Table 13). No significant change of HCA material was observed.

TABLE 13

α-Hexylcinnamic Aldehyde (HCA) Concentration (% w/w) in Samples Stored for 1 Month

| Formulation Code No. | Measured Conc. (% w/w) after Room Temperature Storage | Measured Conc. (% w/w) after Storage at 40° C. |
|---|---|---|
| PG2A | 5.16, 5.20 | — |
| JG6G | 5.60, 5.45 | 5.19, 5.34 |
| AG15B | 5.42, 4.75 | 5.39, 5.35 |
| AG14C | 5.43, 5.76 | 5.25, 4.89 |
| OG3G | 4.82, 4.87 | 5.01, 5.06 |

EXAMPLE 23

Skin Penetration and Evaporation of $^{14}$C-HCA in Formulation

This study was conducted by applying radiolabeled test formulations or control formulations to freshly excised pig skin mounted in skin penetration/evaporation chambers (see Reifenrath, *Cosmetics & Toiletries*, 110, p. 3–11, 1995). Skin penetration and evaporation of radiolabel was determined over a 24 hour period. Radiolabel remaining on the skin surface at 24 hours was determined as the amount removed by 2 tape strips.

Figure 4:
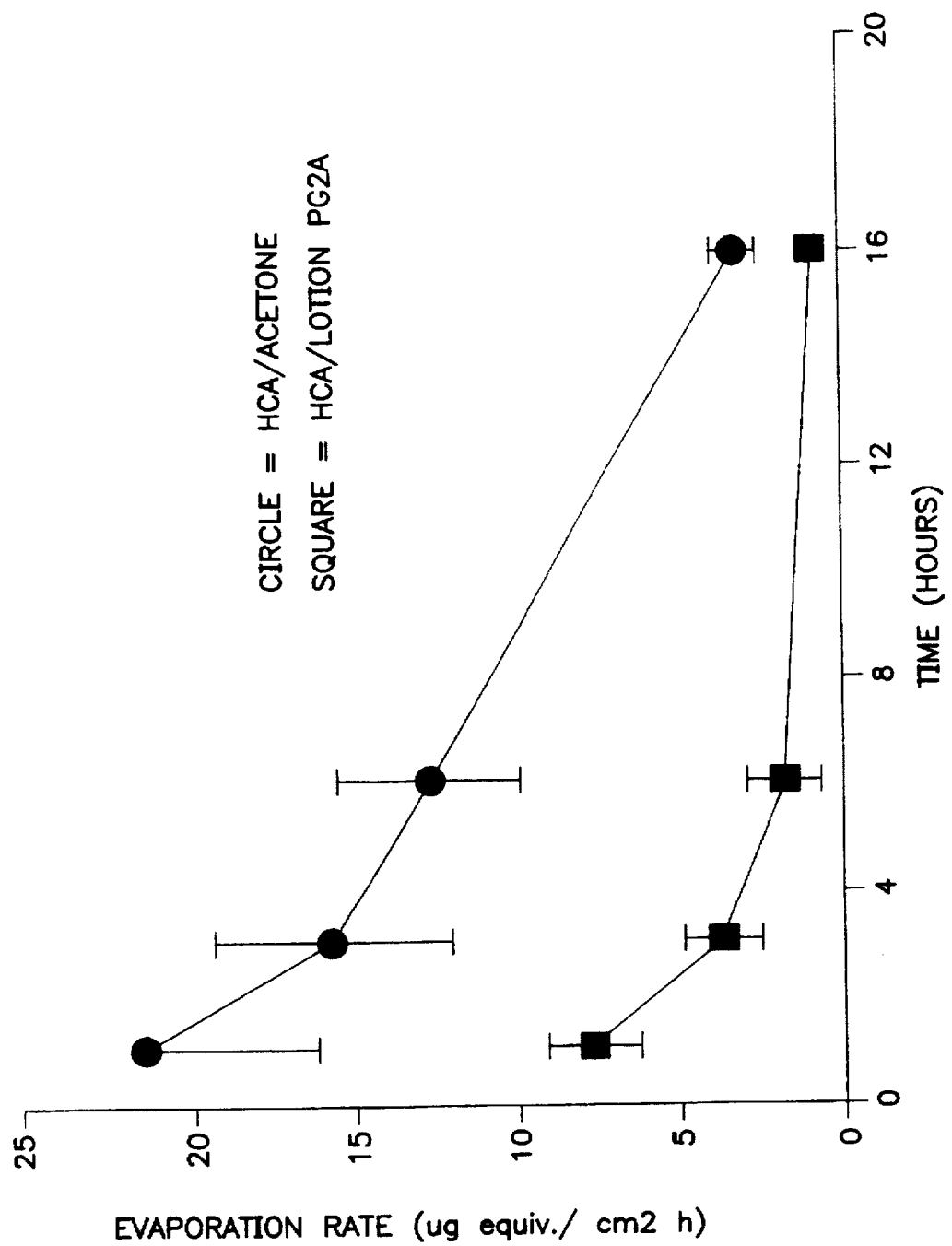
FIG. 4–8 compare the profiles of evaporation of HCA over time from formulations PG2A (FIG. 4), JG6G (FIG. 5), AG15B (FIG. 6), AG14C (FIG. 7) and OG3G (FIG. 8), with the control 5 formulation.
Figure 5:
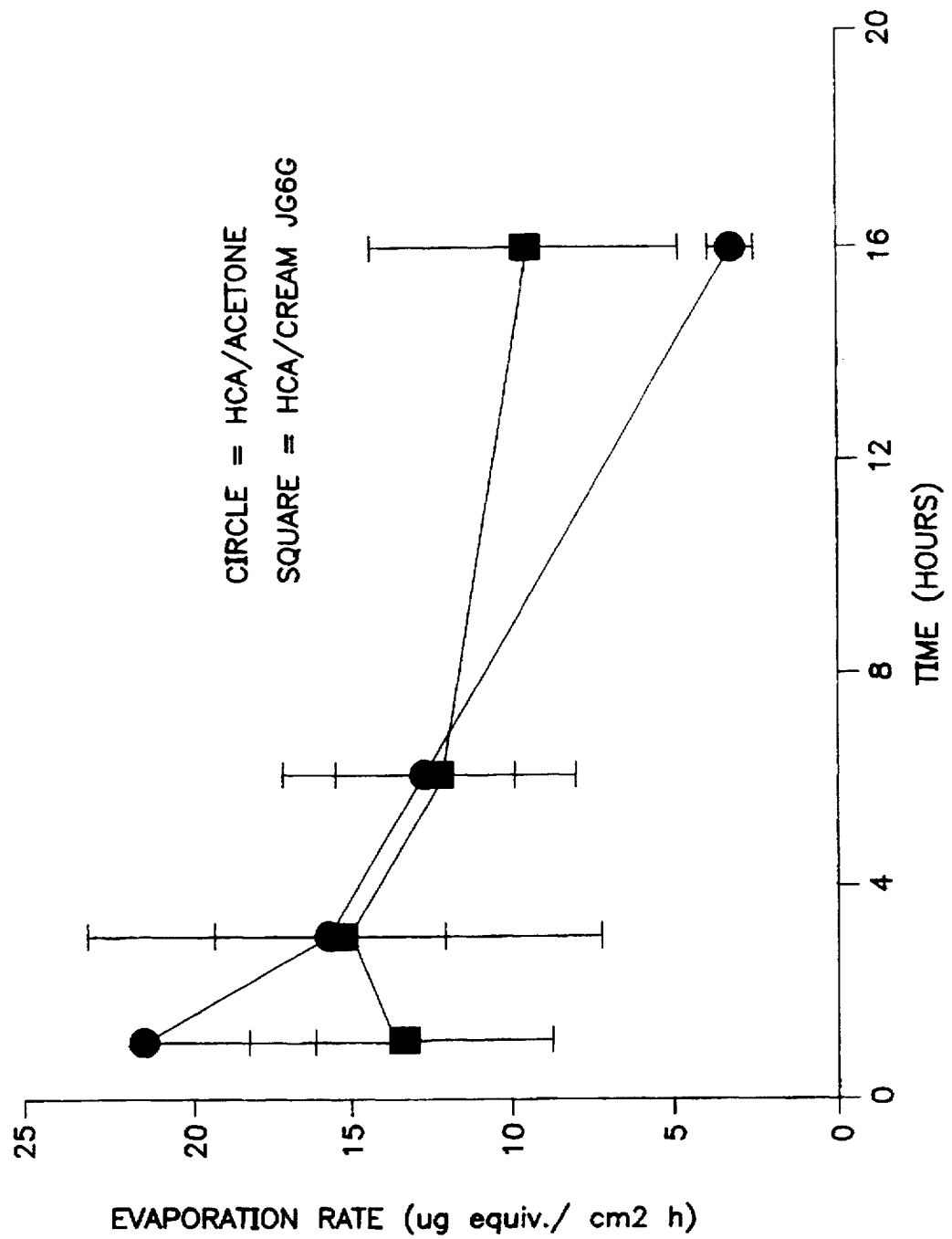
Figure 6:
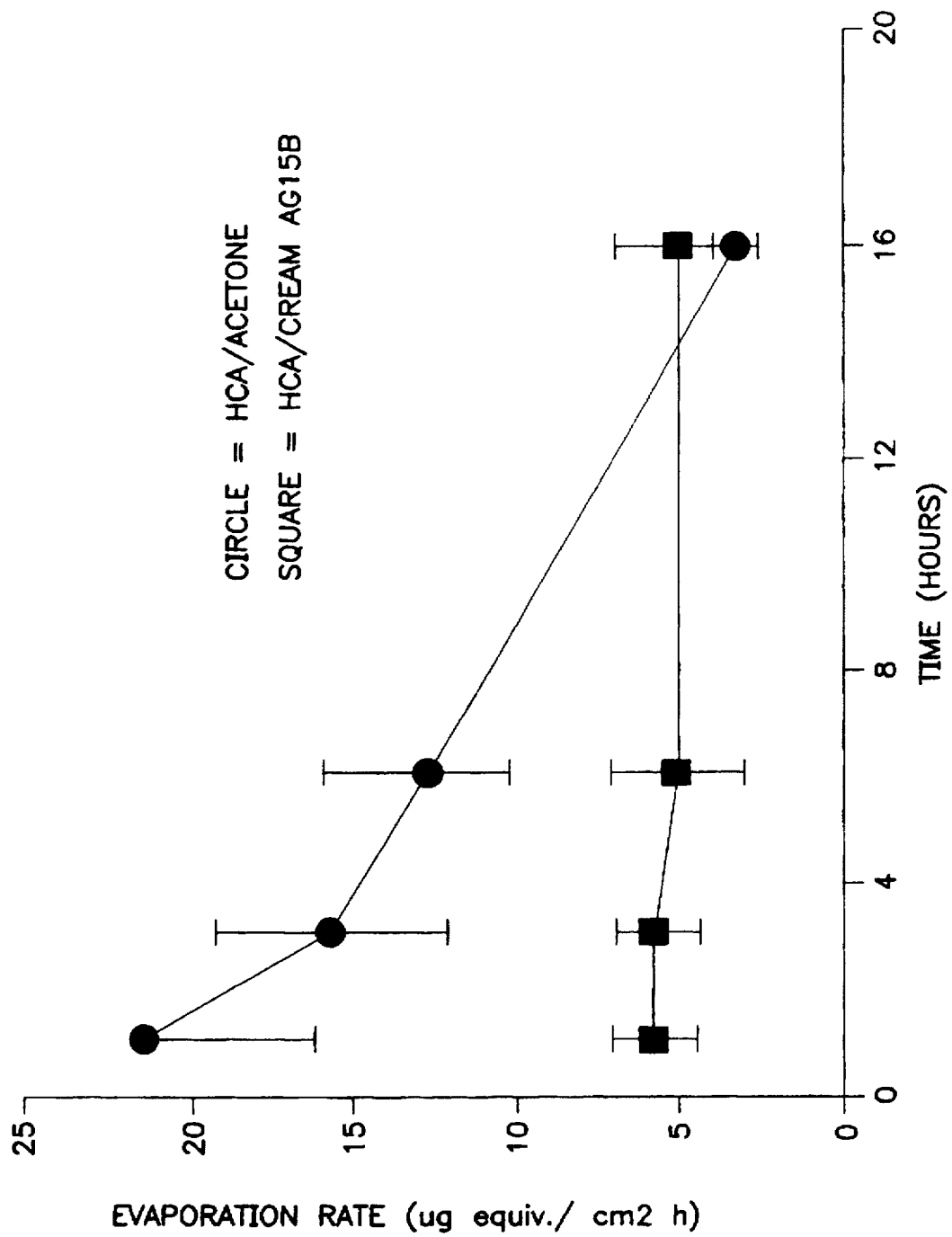
Figure 7:
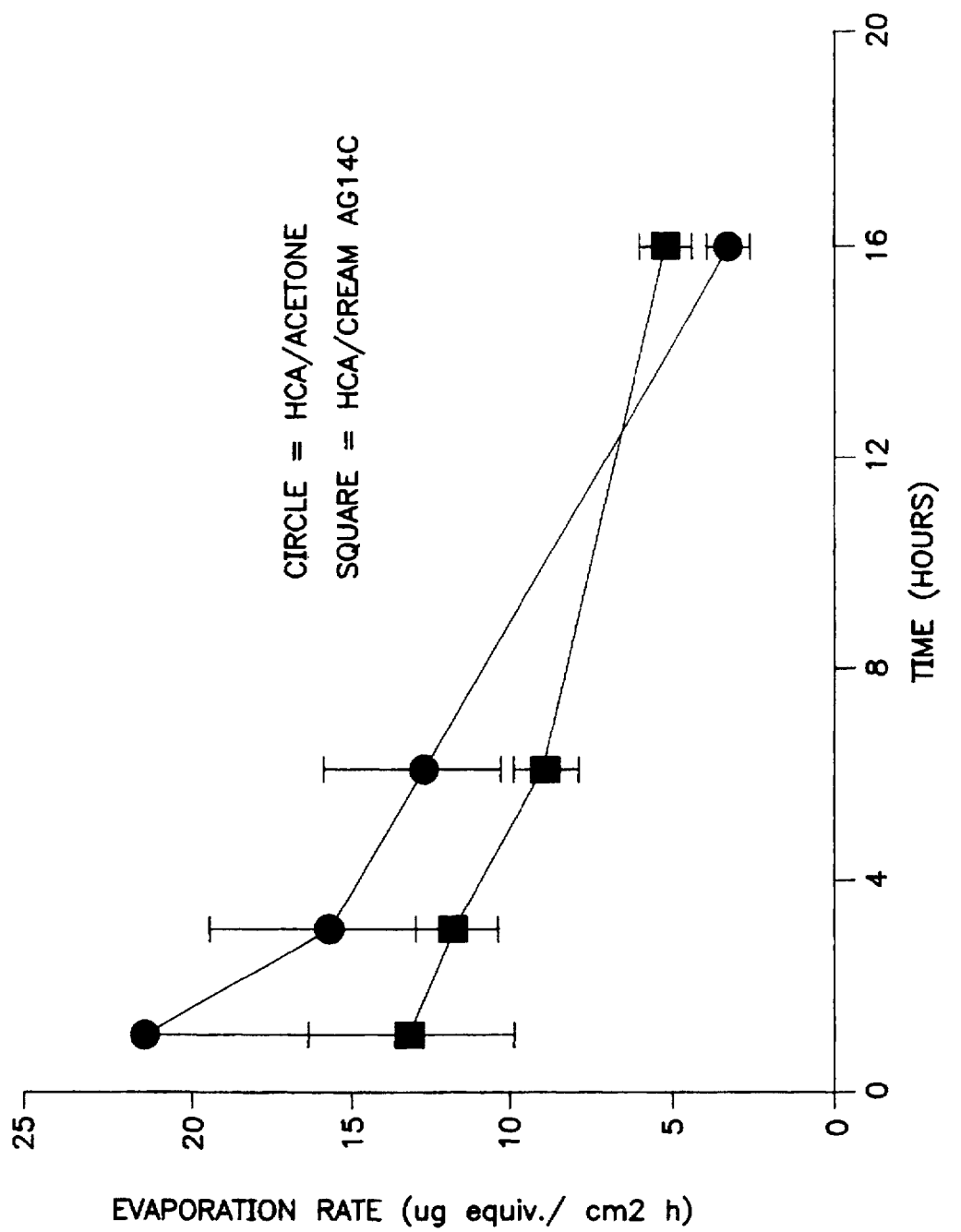

Within 24 hours after receipt of $^{14}$C-HCA, the radiolabel was incorporated into formulations PG2A (RCR F-28), JG6G (RCR F-29), AG15B (RCR F-30), AG14C (RCR F-31) and OG3G (RCR F-32), which were prepared at 5% HCA concentration, and a control formulation containing 5% HCA in acetone. $^{14}$C-HCA, at 2 mCi/mmole specific activity, was added to approximately 750 mg of each formulation to yield a radioactive concentration of approximately 0.1 mCi/5 mg of formulation. Radiolabeled formulations were stored at room temperature. Formulations were prepared to give an approximate dose of 0.3 mg/cm$^2$ when 5 µl or 5 mg of formulation was applied to a skin area of 0.785 cm$^2$. $^{14}$C-HCA gave a radioactive dose of approximately 0.1 mCi and a chemical dose of 0.3 mg/cm$^2$ when 5 µl of solution was applied to 0.785 cm$^2$ area of excised skin. The remaining skin sample was heat separated into epidermis and dermis, which were each assayed for radiolabel. Details of the procedure are as follows:

Freshly harvested, excised pig skin cut with a dermatome to a thickness of approximately 40 to 700 µm was used. This "split-thickness" skin is composed of the epidermis and the outermost portion of the dermis containing the papillary dermis. Twenty-four skin samples selected from four pigs (six samples per pig) were evaluated. The study was conducted as described in Hawkins, G. S. *Methodology for the Execution of In Vitro Skin Penetration Determinations. In: Methods for Skin Absorption*, B. W. Kemppainen and W. G. Reifenrath, Eds., CRC Press, Boca Raton, 1990, pp. 67–80 with the following modifications. Radiolabeled $^{14}$C-HCA formulations were applied to sections of the excised pig skin mounted in the evaporation/penetration chambers. The visceral side of the skin section was bathed by tissue culture medium which served as a sink for radiolabel that penetrated the skin. Sampling of the tissue culture medium during the 24 hour experimental period provided information regarding the time-course of skin penetration. In addition, any test material which evaporated from the skin surface was trapped in Tenax trap above skin surface and measured so that the material balance could be estimated. Twenty-four hours after application of the radiolabeled HCA formulations, excess test material was removed from the epidermal surface of the skin with a cotton wipe and radiolabel remaining in the epidermis and dermis was determined by solubilization and liquid scintillation counting. Since dermal residues would represent compound available for absorption in the in vivo situation, the amount of radiolabel found in the dermis was added to the total amount found in the receptor fluid (fluids in penetration cell) to provide an estimate of human skin absorption. Total evaporation, penetration (sum of radioactivity recovered in the dermis and receptor fluid), and skin surface residue (tape strips) were analyzed by one way analysis of variance for the effect of each formulation on skin penetration. When a significant effect was identified, the formulation was compared to the control ($^{14}$C-HCA in acetone) with Dunnett's test citation. All analyses were carried out at the 0.05 level of significance. The disposition of the radiolabel in isolated pig skin for each formulation is shown in Table 14.

compound, the time course or kinetics of HCA evaporation from the different formulations is even more important. The preferred HCA formulations for mosquito repellency have an evaporation rate that both exceeds the minimum effective evaporation rate (MEER) necessary to repel mosquitoes and is constant over time. In this regard, formulations JG6G (FIG. 5), AG15 B (FIG. 6), and OG3G (FIG. 8) have an essentially constant rate (zero order) of HCA evaporation. Although formulation PG2A significantly reduced total HCA evaporation, the kinetics remained essentially first order (FIG. 4). Formulation AG14C had an evaporation rate vs time profile intermediate between zero and first order (FIG. 7).

EXAMPLE 24

Evaluation of HCA Formulations as Chigger Mite Repellents

Lizards were treated with 5% HCA in control formulation (in Ketone) or four other formulations as specified. The lizards were either thoroughly rubbed with enough liquid material formulation to saturate a common cotton swab twice or thoroughly smeared with enough paste formulation to cover a finger tip. Lizards heavily infested with chigger mites were introduced into the arena of treated populations.

TABLE 14

Disposition of Radiolabeled α-Hexylcinnamic Aldehyde after Application to Excised Pig Skin Mounted

| Formulation | % Application Dose[1] | | | | | |
|---|---|---|---|---|---|---|
| | JG6G | AG15B | AG14C | OG3G | PG2A | Acetone |
| Evaporation | 68 ± 20 | 38 ± 15 | 51 ± 5 | 27 ± 5 | 14 ± 4 | 56 ± 6 |
| Evap. Chamber Rinse plus count of saran over skin during heat separation | 4.1 ± 0.9 | 5.2 ± 1.9 | 6.4 ± 2.0 | 6.2 ± 2.0 | 2.2 ± 1.3 | 10.0 ± 5.0 |
| Tape Strips[2] | 19 ± 13 | 56 ± 10 | 14 ± 10 | 49 ± 9 | 51 ± 6 | 13 ± 3 |
| Epidermis | 6.5 ± 1.8 | 8.8 ± 3.1 | 9.6 ± 3.7 | 7.9 ± 1.7 | 7.6 ± 2.7 | 6.3 ± 3.2 |
| Penetration (Receptor Fluid + Dermis[3]) | 5.0 ± 2.5 | 2.9 ± 1.6 | 7.6 ± 4.8 | 3.2 ± 0.9 | 3.1 ± 3.0 | 7.8 ± 1.9 |
| Total Recovery[4] | 104 ± 7 | 111 ± 7 | 89 ± 4 | 93 ± 7 | 78 ± 9 | 93 ± 5 |

[1] All formulations contained 5% α-hexylcinnamic aldehyde (HCA) and were applied to give an HCA dose of approximately 0.3 mg/cm$^2$. Values represent the mean and standard deviation of 4 replicates, each done with skin from a different pig.
[2] Radioactivity recovered from two successive tape strips of each skin sample.
[3] Radioactivity recovered from the receptor fluid in penetration cell and dermis represented the best estimate of in vivo percutaneous absorption.
[4] Total recovery included small amounts of radioactivity recovered from decontamination of the test apparatus.

Figure 2:
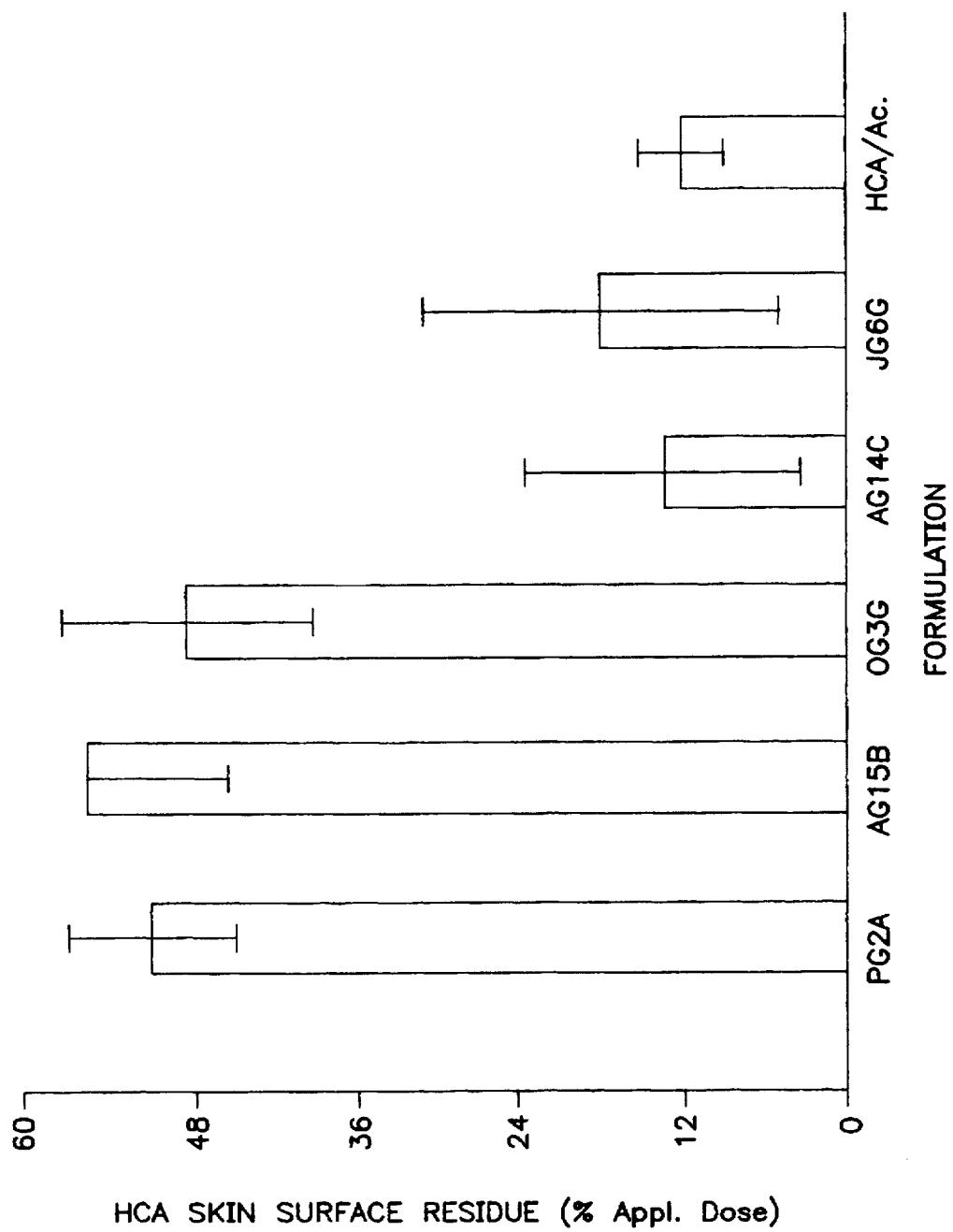
FIG. 2 shows the skin surface residue of the 5 stabilized HCA compositions and the control HCA composition.
Figure 3:
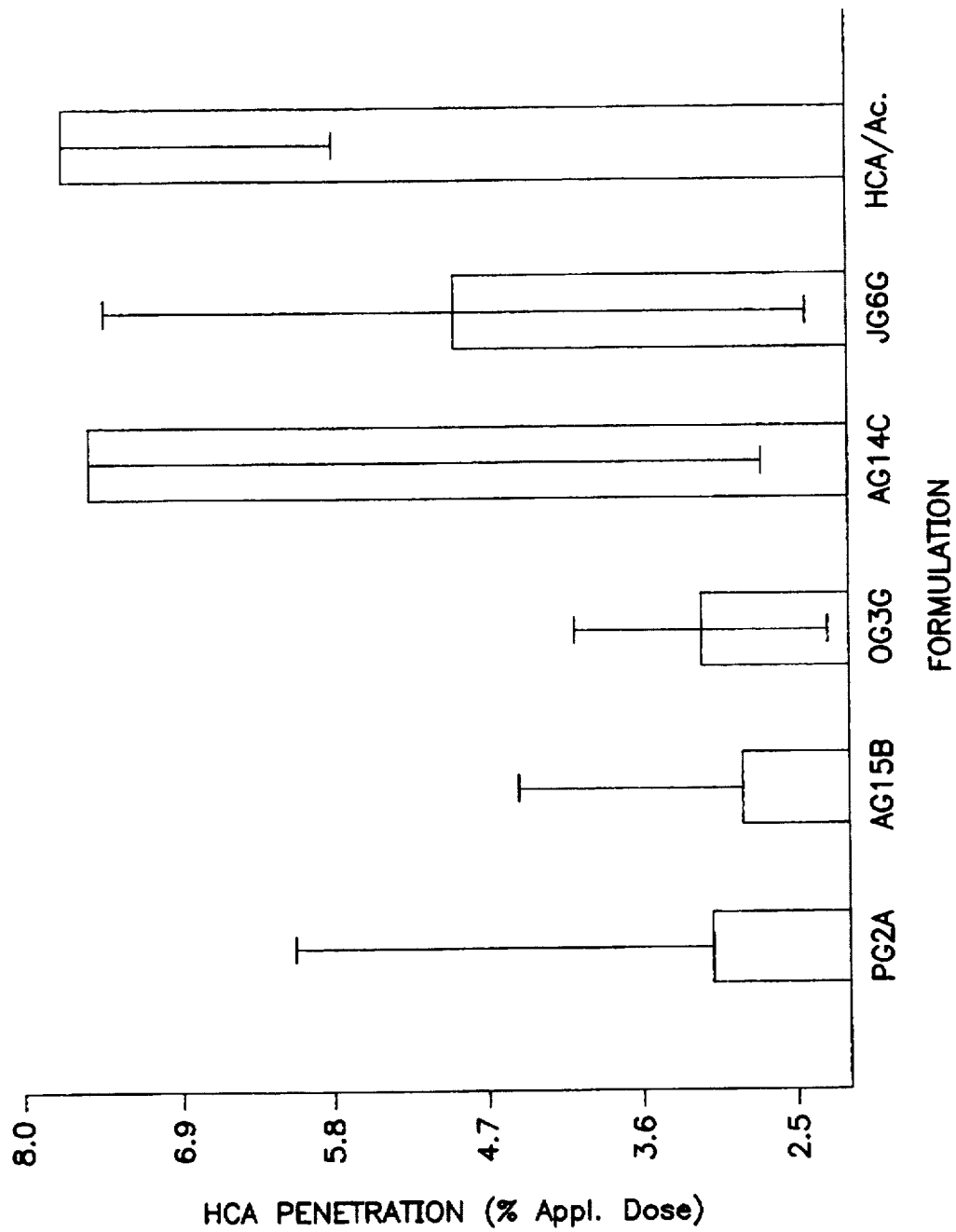
FIG. 3 shows the skin penetration of the 5 stabilized HCA compositions and the control HCA composition.
Figure 8:
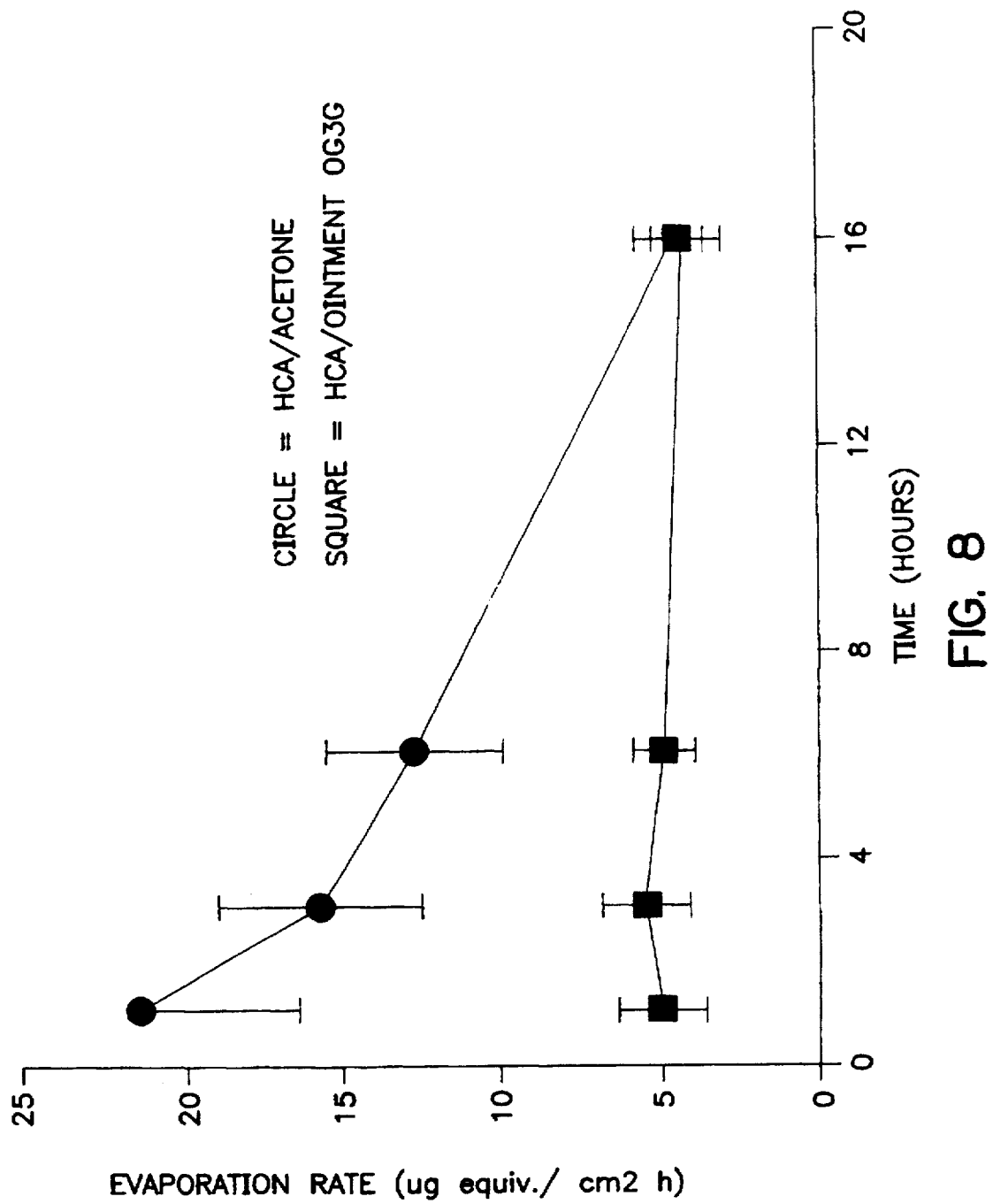

Evaporation, skin surface residue, and skin penetration for the 5 formulations and acetone control are compared in FIGS. 1, 2 and 3 respectively. Profiles of HCA evaporation from each formulations are compared to the control for PG2A (FIG. 4), JG6G (FIG. 5), AG15B (FIG. 6), AG14C (FIG. 7) and OG3G (FIG. 8). Formulations PG2A and OG3G significantly reduced the total evaporative loss of HCA, 14% and 38% respectively, as compared to the acetone control of 50% (Table 12). Formulations PG2A, AG15B, and OG3G significantly increased the HCA skin surface residue (approximately 50% of the applied dose) as compared to the acetone control (13%). Although a significant F (p=0.0511) was not obtained in the analysis of penetration data, all formulations decreased the mean penetration of HCA as compared to the acetone control, particularly formulations PG2A, AG15B and OG3G (Table 12).

While a reduction in total evaporation values for HCA indicate the formulation is exerting some control over the Repellency assays were conducted. Results after one week were recorded and are presented in Table 15.

TABLE 15

Repellent Effects of HCA on Chigger Mites Mean Numbers of Infesting Mites*

| Formulation | Pre-Treatment | Post-Treatment | % of Control |
|---|---|---|---|
| Control | 0 | 10.5 | 100.0 |
| OG3G | 0 | 0.7 | 6.7 |
| AG15B | 0 | 2.5 | 23.8 |
| JG6G | 0 | 1.3 | 12.4 |
| PG2A | 0 | 1.2 | 11.4 |

*Replicates of 10 infested hosts per formulation

The above examples demonstrate that the subject cinnamic aldehyde formulation is effective in repelling phylloxera and mosquitoes; the coniferyl aldehyde formulation is effective to repel thrips; and the α-HCA formulation is effective to repel mosquitoes and mites. The examples also demonstrate that the stabilized composition of α-HCA reduces the evaporation rate of HCA and/or induces a zero order kinetics of HCA evaporation.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

We claim:

1. A composition for repelling a pest from a surface consisting essentially of:

(α-hexylcinnamic aldebyde and one or more stabilizing agent which alters the evaporation rate of α-hexylcimiamic aldehyde from said surface to which said composition is applied, wherein said evaporation rate approximates and exceeds the minimal effective rate necessary to repel said pest from said surface, wherein said stabilizing agent is a polymer selected from the group consisting of ethyl ester of polwviiyi imethyl ether/maleic anhydxide copolymper, polyvinylpyrrolidone/eicosene copolymer, hydrated silica hydrogenated castor oil, dimethicone, mineral oil, polyacrylamide, and isoparaffin, wherein said α-hexyl cinnamic aldehyde and said stabilizing agent are in an amount effective to repel a mosquito or a chigger mite.

2. A composition for repelling a pest from a surface consisting essentially of:

α-hexylcinnamic aldehyde and one or more stabilizing agent which alters the evaporation rate of α-hexylcinnamic aldehyde from said surface to which said composition is applied, wherein said evaporation rate approximates and exceeds the minimal effective rate necessary to repel said pest from said surface, wherein said stabilizing agent is a polyiner selected from the group consisting of ethyl ester of polyvinyl methyl ether/maleic anhydride copolymer, polyvinylpyrrolidone/eicosene copolymer, hydrated silica, hydrogenated castor oil, dimethione, mineral oil, polyacrylamide, and isoparaffin, wherein said α-hexyl cinnarnic aldehyde and said stabilizing agent are in an amount effective to repel a mosquito or a chigger mite, and wherein said composition is non-phytotoxic and non-dermal sensitive.

3. The composition according to claim 1 or 2, wherein less than 40% of said α-hexylcinnamic aldehyde evaporates from said surface in a 24 hour period.

4. The composition according to claim 1 or 2, wherein said evaporation rate is constant over time.

5. The composition according to claim 1 or 2, wherein the total concentration of said one or more stabilizing agent is at least 10% (w/w) of said composition.

6. The composition according to claim 2, wherein said one or more stabilizing agent reduces penetration of said α-hexylcinnamic aldehyde into skin.

7. The composition according to claim 1 or claim 2, wherein said composition is stable when stored at room temperature between 19°–21° C. for at least one month.

8. The composition according to claim 1 or claim 2, wherein said composition is stable at a temperature from 21°–40° C. for at least one month.

9. A method of repelling a pest from the vicinity of a body of a marmmal, said method comprising:

topically applying a composition to a surface in the vicinity of said body selected from the group consisting of skill, furs bair, and clothing, in an amount sufficient to repel said pest, wherein said composition comprises α-hexvl cinnamic aldehyde and one or more stabilizing agent which alters the evaporation rate from a surface to which said composition is applied, wherein said stabilizing agent is a polymer selected from the group consisting of ethyl ester of polyvinyl nmethyl ether/maleic arhydride copolyiner, polyvinylpyrrolidone/eicosene copolymer, hydrated silica, hydrogenated castor oil, dimethicone, mineral oil, polyacrylamide, and isovaraffin, wherein said α-hexyl cinuamic aldehyde and said stabilizing agent are in an amount effective to repel a mosquito or a chigger mite, and wherein said composition is non-phytotoxic and non-dermal sensitive, whereby said pest is repelled from said vicinity.

10. A method of preventing a disease in a mammal, said method comprising:

repelling a pest which is a vector carrying said disease from the vicinity of said miammal's body, according to the method of claim 9, wherein the repellency of said pest is about 100%.

11. The method according to claim 9, wherein said pest is a chigger mite.

12. A method of repelling a pest from a surfaces said method comprising:

topically applying a composition to said surface selected from the group consisting of skin, fuir, hair, and clothing, in an amount sufficient to repel said pest, wherein said composition consists essentially of α-hexyl cinnamic aldehyde and one or more stabilizing agent which alters the evaporation rate from a surface to which said composition is applied, wherein said stabilizing agent is a polymer selected from the group consisting of ethyl ester of polyvinyl methyl ether/maleic anhydride copolymer, polyvinylpyrrolidone/eicosene copolymer, hydrated silica, hydrogenated castor oil, dirnethione, mineral oil, polyacrylanride, and isoparaffin, wherein said α-hexyl cinnamic aldehyde and said stabilizing agent are in an amount effective to repel a mosquito or a chigger mite, whereby said pest is repelled from said vicinity.

* * * * *

UNITED STATES PATENT AND TRADEMARK OFFICE
CERTIFICATE OF CORRECTION

PATENT NO. : 5,792,467

DATED : August 11, 1998

INVENTOR(S) : Emerson et al.

Page 1 of 3

It is certified that error appears in the above-identified patent and that said Letters Patent is hereby corrected as shown below:

On the title page, *Primary Examiner* "Daniel S. Levy" should read --Neil S. Levy--.

Column 1, line 21, delete "," after "for".
Column 1, line 25, "dimethione" should read --dimethicone--.
Column 3, line 19, insert --(1)-- in the right margin to reflect the appropriate reference to the Figure.
Column 4, line 9, "compounding" should read --compound in--.
Column 4, line 58, "fimctional" should read --functional--.
Column 5, line 60, "fimgi" should read --fungi--.
Column 6, line 5, insert --(2)-- in the right margin to reflect the appropriate reference to the Figure.
Column 6, line 43, add --(5)-- in the right margin to reflect the appropriate reference to the Figure.
Column 8, line 31, "same" should read --some--.
Column 11, line 14, "flugal" should read --fungal--.
Column 12, line 15, "finctions" should read --functions--.
Column 12, line 27, "cinhnamic" should read --cinnamic--.
Column 17, line 6, "finctions" should read --functions--.
Column 22, line 27, "Leaflioppers (*Cicade/lidae*) should read --Leafhoppers (*Cicadellidae*)--.
Column 23, line 39, "Sipider" should read --Spider--.
Column 24, line 11, "in I ml" should read --in 1 ml--.
Column 26, line 51, delete "[most organisms?]".
Column 27, line 4, "selecter" should read --selected--.
Column 27, line 23, "*Aegpti*" should read --*Aegypti*--.
Column 27, line 27, "*Aegypsi*" should read --*Aegypti*--.
Column 29, line 29, "(AG15 SB)" should read --(AG15B)--.
Column 31, line 31, delete "(".
Column 32, line 2, "x" should read --for--.
Column 35, line 57, "38%" should read --27%--.

UNITED STATES PATENT AND TRADEMARK OFFICE
CERTIFICATE OF CORRECTION

PATENT NO. : 5,792,467

DATED : August 11, 1998

INVENTOR(S) : Emerson et al.

It is certified that error appears in the above-identified patent and that said Letters Patent is hereby corrected as shown below:

Column 35, line 58, "50% (Table 12)" should read --56% (Table 14)--.
Column 35, line 65, "(Table 12)" should read --(Table 14)--.
Column 36, line 24, "fmger" should read --finger--.
Claim 1, line 3, "aldebyde" should read --aldehyde--.
Claim 1, line 3, delete "(".
Claim 1, line 5, "α-hexylciniamic" should read --α-hexylcinnamic--.
Claim 1, line 10, "polwviiyi" should read --polyvinyl--.
Claim 1, line 11, "imethyl" should read --methyl--.
Claim 1, line 11, "amhydxide" should read --anhydride--.
Claim 1, line 11, "copolymper" should read --copolymer--.
Claim 1, line 13, add "," after "silica".
Claim 2, line 9, "polyiner" should read --polymer--.
Claim 2, line 13, "dimethione" should read --dimethicone--.
Claim 2, line 15, "cinnamic" should read --cinnamic--.
Claim 9, line 2, "marmmal" should read --mammal--.
Claim 9, line 5, "skill, furs bair," should read --skin, fur, hair,--.
Claim 9, line 7, "α-hexvl" should read --α-hexyl--.
Claim 9, line 11, "nmethyl" should read --methyl--.
Claim 9, line 12, "copolyiner" should read --copolymer--.
Claim 9, line 12, "arhydride" should read --anhydride--.
Claim 9, line 15, "isovaraffin" should read --isoparaffin--.
Claim 9, line 15, "cinuamic" should read --cinnamic--.

UNITED STATES PATENT AND TRADEMARK OFFICE
CERTIFICATE OF CORRECTION

PATENT NO.  : 5,792,467
DATED       : August 11, 1998
INVENTOR(S) : Emerson et al.

It is certified that error appears in the above-identified patent and that said Letters Patent is hereby corrected as shown below:

Claim 10, line 4, "miammal's" should read --mammal's--.
Claim 12, line 1, "surfaces" should read --surface--.
Claim 12, line 4, "fuir" should read --fur--.
Claim 12, line 14, "dimethione" should read --dimethicone--.
Claim 12, line 14, "polyacrylanride" should read --polyacrylamide--.

Signed and Sealed this

Twenty-third Day of March, 1999

Q. TODD DICKINSON

Attest:

Attesting Officer

Acting Commissioner of Patents and Trademarks